(12) United States Patent
Sakurai et al.

(10) Patent No.: US 7,659,273 B2
(45) Date of Patent: Feb. 9, 2010

(54) COMPOSITION FOR ACCELERATING BONE FRACTURE HEALING

(75) Inventors: Naoki Sakurai, Solana Beach, CA (US); Toshiki Takagi, Itami (JP); Noriyuki Yanaka, Higashihiroshima (JP); Yuji Horikiri, Kawanishi (JP); Takashi Tamura, Amagasaki (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 353 days.

(21) Appl. No.: 11/826,921

(22) Filed: Jul. 19, 2007

(65) Prior Publication Data

US 2008/0031958 A1 Feb. 7, 2008

Related U.S. Application Data

(62) Division of application No. 10/478,709, filed as application No. PCT/JP02/04931 on May 22, 2002, now abandoned.

(30) Foreign Application Priority Data

May 23, 2001 (JP) ............................. 2001-154064

(51) Int. Cl.
*A61K 31/495* (2006.01)
*A61K 31/435* (2006.01)
*A61K 31/38* (2006.01)

(52) U.S. Cl. .................... 514/248; 514/277; 514/438
(58) Field of Classification Search .............. 514/248, 514/277, 438
See application file for complete search history.

(56) References Cited

U.S. PATENT DOCUMENTS

| | | | |
|---|---|---|---|
| 4,193,926 A | 3/1980 | Schmiechen et al. |
| 4,542,025 A | 9/1985 | Tice et al. |
| 5,000,886 A | 3/1991 | Lawter et al. |
| 5,171,217 A | 12/1992 | March et al. |
| 5,223,504 A | 6/1993 | Noverola et al. |
| 5,288,496 A | 2/1994 | Lewis et al. |
| 5,294,446 A | 3/1994 | Schlameus et al. |
| 5,503,851 A | 4/1996 | Mank et al. |
| 5,552,438 A | 9/1996 | Christensen, IV |
| 5,605,914 A | 2/1997 | Muller |
| 5,614,515 A | 3/1997 | Rodgers et al. |
| 5,804,588 A | 9/1998 | Dyke et al. |
| 5,910,492 A | 6/1999 | Hoshino et al. |
| 5,922,253 A | 7/1999 | Herbert et al. |
| 5,939,388 A | 8/1999 | Rosen et al. |
| 6,010,711 A | 1/2000 | O'Keefe et al. |
| 6,011,060 A | 1/2000 | Laurent et al. |
| 6,197,326 B1 | 3/2001 | Suzuki et al. |
| 6,214,008 B1 | 4/2001 | Illi |
| 6,451,335 B1 | 9/2002 | Goldenheim et al. |

| | | |
|---|---|---|
| 2002/0123520 A1 | 9/2002 | Marfat et al. |

FOREIGN PATENT DOCUMENTS

| | | |
|---|---|---|
| CA | 2 278 217 | 11/1998 |
| DE | 100 61 137 | 6/2002 |
| EP | 0 158 380 A1 | 10/1985 |
| EP | 0 163 965 A2 | 12/1985 |
| EP | 0 251 476 | 1/1988 |
| EP | 0 260 817 A1 | 3/1988 |
| EP | 0 432 856 A3 | 6/1991 |
| EP | 0 459 505 A1 | 12/1991 |
| EP | 0 497 564 A1 | 8/1992 |
| EP | 0 557 016 A1 | 8/1993 |
| EP | 0 403 383 B1 | 8/1994 |
| EP | 0 623 607 A1 | 11/1994 |
| EP | 0 738 715 A2 | 10/1996 |
| EP | 0 748 805 A1 | 12/1996 |
| EP | 0 781 548 | 7/1997 |
| EP | 0 848 000 A1 | 6/1998 |
| EP | 0 911 025 A1 | 4/1999 |
| EP | 1 053 746 | 11/2000 |
| EP | 1 308 440 | 5/2003 |
| JP | 56-19324 | 5/1981 |
| JP | 60-67417 | 4/1985 |
| JP | 60-100516 | 6/1985 |
| JP | 62-201816 | 9/1987 |
| JP | 63-091325 | 4/1988 |
| JP | 1-155942 | 6/1989 |

(Continued)

OTHER PUBLICATIONS

Bostrom, Mathias, MD, et al., "Use of Bone Morphogenetic Protein-2 in the Rabbit Ulnar Nonunion Model," Clinical Orthopaedics and Related Research, No. 327, 1996, pp. 272-282.
Japanese Office Action dated Feb. 3, 2009, issued in Japanese Patent Application No. 2002-591037, 3 pp.
Janetti N. Francischi et al., "Anti-inflammatory and analgesic effects of the phosphodiesterase 4 inhibitor rolipram in a rat model of arthritis," European Journal of Pharmacology, 399 (2000) 243-249.
Shohei Kasugai et al., "Potential of PDE4 Inhibitors in the Treatment of Osteopenia," Drug News Perspect 12(9), Nov. 1999.
Shohei Kasugai et al., "Anabolic effect of a phosphodiesterase 4 (PDE4) inhibitor in bone and its possible mechanism," Jpn. J. of Pharmacol 79, Suppl. 1, 277 (1999).

(Continued)

*Primary Examiner*—Raymond J Henley, III
(74) *Attorney, Agent, or Firm*—Finnegan, Henderson, Farabow, Garrett & Dunner, L.L.P.

(57) ABSTRACT

A composition for accelerating fracture healing, which has a PDE4 inhibitor as an active ingredient, specifically a composition having a PDE4 inhibitor and a biocompatible and biodegradable polymer is provided, which composition, when formulated into a form suitable for local administration such as a microsphere preparation, can provide a pharmaceutical composition showing an excellent effect in the early healing of bone fracture. The composition is useful in healing of refractory fracture of elderly people and diabetic or osteoporosis patients.

21 Claims, 9 Drawing Sheets

FOREIGN PATENT DOCUMENTS

| | | |
|---|---|---|
| JP | 01-305929 | 12/1989 |
| JP | 4-364179 | 12/1992 |
| JP | 5-58882 | 3/1993 |
| JP | 5-70363 | 3/1993 |
| JP | 5-194200 | 8/1993 |
| JP | 5-229987 | 9/1993 |
| JP | 6-32732 | 2/1994 |
| JP | 6-211648 | 8/1994 |
| JP | 6-305983 | 11/1994 |
| JP | 07 101861 | 4/1995 |
| JP | 8-151321 | 6/1996 |
| JP | 9-59255 | 3/1997 |
| JP | 9-110678 | 4/1997 |
| JP | 09-169665 | 6/1997 |
| JP | 9-221417 | 8/1997 |
| JP | 9-221418 | 8/1997 |
| JP | 9-263545 | 10/1997 |
| JP | 10-158267 | 6/1998 |
| JP | 10-182499 | 7/1998 |
| JP | 10-226685 | 8/1998 |
| JP | 2001-198208 | 7/2001 |
| WO | WO 90/09783 | 9/1990 |
| WO | WO 91/01720 | 2/1991 |
| WO | WO 91/16314 | 10/1991 |
| WO | WO 92/12961 | 8/1992 |
| WO | WO 92/15282 | 9/1992 |
| WO | WO 93/09118 | 5/1993 |
| WO | WO 94/02465 | 2/1994 |
| WO | WO 94/22852 | 10/1994 |
| WO | WO 94/25437 | 11/1994 |
| WO | WO 95/00516 | 1/1995 |
| WO | WO 95/04045 | 2/1995 |
| WO | WO 95/08534 | 3/1995 |
| WO | WO 95/14667 | 6/1995 |
| WO | WO 95/14681 | 6/1995 |
| WO | WO 95/20578 | 8/1995 |
| WO | WO 95/35282 | 12/1995 |
| WO | WO 96/00215 | 1/1996 |
| WO | WO 96/00218 | 1/1996 |
| WO | WO 96/06843 | 3/1996 |
| WO | WO 96/20698 | 7/1996 |
| WO | WO 96/28143 | 9/1996 |
| WO | WO 96/31485 | 10/1996 |
| WO | WO 97/13502 | 4/1997 |
| WO | WO 97/18208 | 5/1997 |
| WO | WO 97/22585 | 6/1997 |
| WO | WO 97/22586 | 6/1997 |
| WO | WO 97/23457 | 7/1997 |
| WO | WO 97/23547 | 7/1997 |
| WO | WO 97/29750 | 8/1997 |
| WO | WO 97/40032 | 10/1997 |
| WO | WO 97/44036 | 11/1997 |
| WO | WO 97/44322 | 11/1997 |
| WO | WO 98/02440 | 1/1998 |
| WO | WO 98/09961 | 3/1998 |
| WO | WO 98/11113 | 3/1998 |
| WO | WO 98/13348 | 4/1998 |
| WO | WO 98/14432 | 4/1998 |
| WO | WO 98/31674 | 7/1998 |
| WO | WO 98/56431 | 12/1998 |
| WO | WO 99/23076 | 5/1999 |
| WO | WO 99/47186 | 9/1999 |
| WO | WO 99/50270 | 10/1999 |
| WO | WO 99/65474 | 12/1999 |
| WO | WO 00/50011 | 8/2000 |
| WO | WO 00/66584 | 11/2000 |
| WO | WO 01/13953 | 3/2001 |
| WO | WO 01/45705 A1 | 6/2001 |
| WO | WO 01/46136 | 6/2001 |
| WO | WO 01/55112 | 8/2001 |
| WO | WO 01/57025 | 8/2001 |
| WO | WO 01/76575 A2 | 10/2001 |
| WO | WO 01/80835 A1 | 11/2001 |
| WO | WO 01/83594 A1 | 11/2001 |
| WO | WO 01/93909 | 12/2001 |
| WO | WO 02/14280 | 2/2002 |
| WO | WO 02/060875 | 8/2002 |
| WO | WO 02/060898 | 8/2002 |

OTHER PUBLICATIONS

Ken-ichi Miyamoto et al., Reduction of Bone Loss by Denbufylline, an Inhibitor of Phosphodiesterase 4, Biochemical Pharmacology, 1997, vol. 54, No. 5, 613-617.
Yoshihiro Waki et al., "Effects of XT-44, a Phosphodiesterase 4 Inhibitor, in Osteoblastgenesis and Osteoclastgenesis in Culture and Its Therapeutic Effects in Rat Osteopenia Models," Jpn. J. Pharmacol. 79, 477-483 (1999).
T. Kinoshita, "Phosphodiesterase Inhibitors, Pentoxifylline and Rolipram, Increase Bone Mass Mainly by Promoting Bone Formation in Normal Mice,"Bone, vol. 27, No. 6 (Dec. 2000) 811-817.
Hitoshi Sezaki, "Drug Delivery System," Nankodo Co., Ltd. 1986, 185-189 w/trans. p. 185-line 11 to p. 187-line 12.
J. Jpn. Orthop. Assoc. 74(8) 2000 S-1737, S-1735, S-1330, S-1814 with English translations.
J. Jpn. Orthop. Assoc. 73(8) 199 S-1519 with English translations.
Exp. Toxicol. Pathol 45(8) 473-479 (1993/94).
Journal of Bone and Mineral Metabolisum vol. 17(2) 202 (1999) with English translation.
J. Bone and Mineral Res. 14 (Suppl. 1) S349 (1999).
J. Bone and Mineral Res. 14 (Suppl. 1) S354 (1999).
J. Bone and Mineral Res. 14 (Suppl. 1) S504 (1999).
Igaku-Daijiten, 18th Ed., published by Nanzando, pp. 719-720-P1.
Kossetsu Chiryougaku (Fracture Therapeutics), Apr. 2000, pp. 29-37, 46-51, Nanko-do-P2 with English translation.
Proc. Natl. Acad. Sci. USA vol. 87, p. 2220-2224 (1990).
Trends in Pharmacological Sciences, Vo. 11. p. 150-155 (1990).
Advances in Cyclic Nucleotide Research vol. 10, p. 69-92 (1979).
Cellular Signaling vol. 9, Issues 3-4, p. 227-236 (1997).
Journal of Controlled Release 59 p. 77-86 (1999).
Journal of Controlled Release 33 p. 237-243 (1995).
Biomaterials vol. 21 p. 2405-2412 (2000).
International Journal of Pharmaceutics vol. 206 p. 1-12 (2000).
Drug Development and Industrial Pharmacy vol. 24(8) p. 703-727 (1998).
European J. Pharm. Biopharm. vol. 42(1) p. 16-24 (1996).
Spray Drying Handbook (1984).
Microcapsulation and Related Drug Processes (1984).
International Journal of Pharmaceutics vol. 187, p. 143-152 (1999).
U.S. Appl. No. 10/478,432, filed Nov. 21, 2003.
Journal of China Pharmaceutical University, vol. 30, No. 1 (Jan. 1999) and its English translation thereof.
H. Horiuchi et al., "Enhancement of Bone Morphogenetic Protein-2-Induced New Bone Formation in Mice by the Phosphodiesterase Inhibitor Pentoxifylline," Bone vol. 28, No. 3, Mar. 2001, pp. 290-294, XP-002389298.
Hazel J. Dyke et al, "The therapeutic potential of PDE4 inhibitors," Expert Opinion on Investigational Drugs, Ashley Publications Ltd., London, GB, vol. 8, No. 9, 1999, pp. 1301-1325 XP-001096074.
H. Horiuchi et al., "Effect of Phosphodiesterase Inhibitor-4, Rolipram, on New Bone Formations by Recombinant Human Bone Morphogenetic Protein-2," Bone vol. 30, No. 4, Apr. 2002, pp. 589-593, XP-002389299.
Norman, "PDE4 Inhibitors 1998," Expert Opinion on Therapeutic Patents, vol. 8, No. 7, 1998, pp. 771-784.
Chambers et al., "Biarylcarboxamide Inhibitors of Phosphodiesterase IV and Tumor Necrosis Factor-α," Bioorganic and Medicinal Chemistry Letters, vol. 7, No. 6, 1997, pp. 739-744.
Lambrecht et al., "Design of Rolipram-Loaded Nanoparticles: Comparison of Two Preparation Methods," Journal of Controlled Release, Elsevier, vol. 71, No. 3, Apr. 28, 2001, pp. 297-306.

Kasugai et al., "Phosphodiesterase IV Inhibitor (Rolipram) Stimulates Osteoblastic Differentiation in Rat Bone Marrow Cell Culture," Japanese J. of Pharma., J. Pharma. Soc., vol. 73, No. Supp. 1, 1997, pp. 289P, AbstractP-685.

Lambrecht et al., "Biodegradable Nanoparticles for Targeted Drug Delivery in Treatment of Inflammatory Bowel Disease, "J. of Pharma. and Experimental Therapeutics, vol. 299, No. 2, 2001, pp. 775-781.

Supplementary Partial European Search Report, Application No. 02771772.7-2107, PCT/JP0204931, dated Dec. 12, 2006, 33 pages.

Communication from European Patent Office in EP Application 02 771 772.7, May 16, 2007, 5 pages.

International Search Report, PCT/JP02/04930, Aug. 27, 2002.

Communication from European Patent Office in EP Application 02 771 771.9, May 8, 2007, 4 pages.

Shapiro et al., "Cell origin and differentiation in the repair of full-thickness defects of articular cartilage," Journal of Bone and Joint Surgery, Series A, vol. 75(4), pp. 532-553, 1993.

Tenor, Hermann et al., "Phosphodiesterase isoenzyme familes in human osteoarthristis chondrocytes-functional importance of phosphodiesterase 4," British Journal of Pharmacology, (2002) vol. 135, No. 3 pp. 609-618.

Kaminuma et al., "A selective type 4 phosphodiesterase inhibitor, T-440, modulates intracellular cyclic AMP level and interleukin-2 production of Jurkat cells," Immunopharmacology, vol. 38, No. 3, pp. 247-252, 1998.

Japanese Office Action dated May 7, 2008, issued in Japanese Patent Application No. 2002-591037, 4 pp.

Delgado-Martínez, A.D. et al., "Effect of 25-OH-Vitamin D on Fracture Healing in Elderly Rats," Journal of Orthopaedic Research, vol. 16, No. 6, 1998, pp. 650-653.

Sanchez-Sotelo, J. et al., "Treatment of Fractures of the Distal Radius With a Remodellable Bone Cement a Prospective, Randomised Study Using Norian SRS," The Journal of Bone and Joint Surgery, vol. 82, No. 6, 2000, pp. 856-863.

Babicky, A. et al., "Effect of Calcitonin on Fracture Healing in Rats," Endocrinol Exp., vol. 10, No. 1, 1976) p. 73 (Abstract).

Japanese Office Action dated Nov. 17, 2009, issued in Japanese Patent Application No. 2002-591037, 3 pp.

COMPOSITION FOR ACCELERATING BONE FRACTURE HEALING

This is a division of application Ser. No. 10/478,709, filed Nov. 24, 2003, now abandoned, which is a § 371 of PCT/JP02/04931, filed May 22, 2002, which claims benefit of priority to Japanese Application 2001-154064, filed May 23, 2001, all of which are incorporated herein by reference.

TECHNICAL FIELD

The present invention relates to a composition for accelerating bone fracture healing, specifically, to a pharmaceutical composition for accelerating bone fracture healing, which comprises as an active ingredient a PDE4 inhibitor, preferably a PDE4 inhibitor together with a biocompatible and biodegradable polymer, which is especially in the form of microsphere preparation, more preferably, microsphere-containing injectable preparation, and which is able to promote bone fracture healing when locally administered.

BACKGROUND ART

Bone fracture is a condition where a physiological continuity of bone tissue is partially or completely broken off and generally classified on the basis of the outbreak mechanism into (a) fracture by external force, (b) pathological fracture, and (c) fatigue fracture. In addition, the state of bone fracture is classified on the basis of the fracture line (the line tracing the epiphysis generated by bone transection), into fissure fracture, greenstick fracture, transverse fracture, oblique fracture, spiral fracture, segmental fracture, comminuted fracture, avulsion fracture, compression fracture, depression fracture, and the like (IGAKU-DAIJITEN, 18th ed., pp. 719-720, published by Nanzando).

Generally, it takes a considerable time until a bone fracture heals, which can be an obstacle in daily life. Further, the number of bone fracture of the osteoporosis patients, which is one of pathological fractures, has markedly increased with the aging of population. In particular, the transcervical fracture requires a long-term hospitalization and often develops internal complication including dementia due to a long-term hospitalization, which is becoming a major social and economic issue.

The fracture healing process is mainly classified into the following three stages ("Kossetsu Chiryougaku (Fracture Therapeutics)", April, 2000, pp. 29-37, 46-51, Nanko-do), and it is considered that, the healing progresses in the reparative phase, an important stage for bone fracture healing, by a mechanism different from that in the bone remodeling phase where osteogenesis and osteolysis (bone resorption) occur repeatedly.

(1) An inflammatory phase: tissue surrounding bone is damaged, a fracture crevice is occupied with hematoma, and inflammation arises at the fracture region.

(2) A reparative phase: two processes progress in parallel; a process in which hematoma in the fracture crevice is removed yielding granulation tissue, soft callus is formed and gradually replaced by hard callus via osteogenic mechanism (endochondral ossification), and a process in which a new bone is formed by osteogenic cells present in periost (fibrous/intramembraneous ossification).

(3) A re-molding phase: the formed new bone extends for a long term by repeating the bone resorption and the bone formation, while the bone deformation is corrected and defect region reinforced.

The new bone formed during the re-molding phase has intensity of certain degree, and one's daily life is less hampered; however, the reparative phase takes a long term and restricts patient's daily life greatly. Accordingly, it is clinically important to shorten the term of reparative phase.

As substances accelerating bone fracture healing, there have been disclosed peptide-type physiologically active substances such as bone morphogenetic protein (BMP) and transforming growth factor (TGF) (Proc. Natl. Acad. Sci., USA, vol. 87, pp. 2220-2224 (1989). Further, it has been disclosed a pharmaceutical preparation for local administration containing a compound of the formula below (JP-04-364179A (1992)) as a bone formation accelerator after microcapsulation with lactic acid-glycolic acid copolymer (PLGA) in JP-09-263545A (1997).

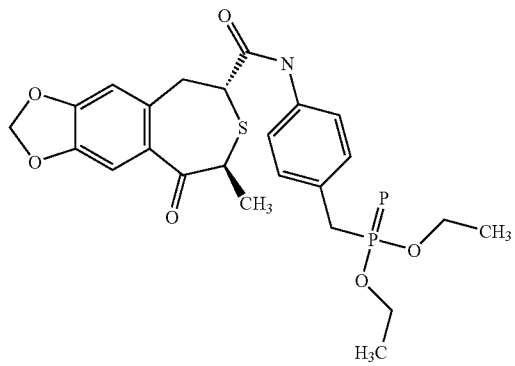

The possibility of improving the bone mass by increasing the intracellular cyclic AMP (cAMP) level with phosphodiesterase (PDE) inhibitor was studied, and it was reported that the increase of bone mineral density of the backbone and the femur, and hyperplasia of cortical bone were observed in a mouse received daily subcutaneous injection of Pentoxifylline, a general PDE inhibitor, or Rolipram that is a selective PDE4 inhibitor (Bone, vol. 27, 6th issue, pp. 811-817 (2000)).

However, the researches above are focused on the pharmacological effect on a normal region, which is an osteogenic region during re-modeling process, and not a bone fracture region and are totally silent about bone fracture healing accelerating activity of PDE4 inhibitor.

DISCLOSURE OF INVENTION

One of purposes of the present invention is to provide a novel pharmaceutical composition for accelerating bone fracture healing, which accelerates the healing of a fracture in the early stage. Another purpose of the present invention is to provide a novel pharmaceutical composition for local administration which, when applied to a fracture region, exerts efficiently the fracture healing accelerating activity only at an intended site while avoiding the manifestation of systemic action of an active ingredient. Yet another purpose of the present invention is to provide a sustained release depot preparation for accelerating bone fracture healing, which, when applied locally, can release an active ingredient gradually and exert the drug efficacy over a long term by one time dosage.

The present inventors have investigated into pharmacological actions of various compounds and noticed that compounds having PDE4 inhibiting activity could affect the fracture healing process. The inventors have then found that the compounds having PDE4 inhibiting activity can accelerate the fracture healing and established the present invention.

The present invention provides a composition for accelerating bone fracture healing, which comprises a PDE4 inhibitor as an active ingredient. In particular, the present invention provides a pharmaceutical preparation suitable for local administration at the fracture region, specifically, a bone fracture healing accelerating composition in the form of depot preparation.

BEST MODE FOR CARRYING OUT THE INVENTION

Figure 1:
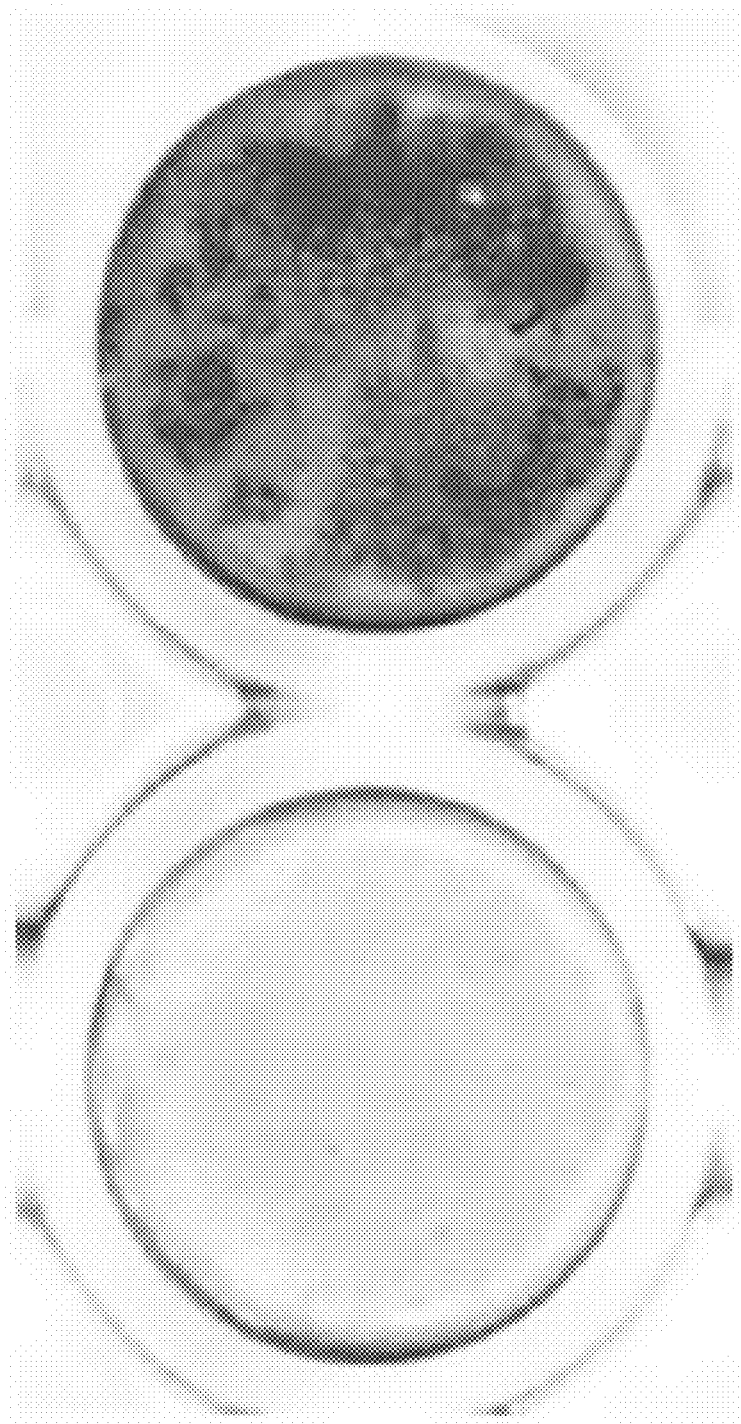
FIG. 1 is a copy of photography showing chondrocyte calcification (calcium deposits) effect of Compound (1) in cultured rabbit costicartilage cells.

The bone fracture healing accelerating composition of the present invention has a superior effect on the bone fracture healing process especially in the reparative phase. The present composition can accelerate the fracture healing by accelerating the endochondral ossification wherein a soft callus is formed at the fracture region, which in turn is replaced by hard callus.

The pharmaceutical composition of the present invention can be prepared by combining a PDE4 inhibitor as an active ingredient and a conventional pharmaceutically acceptable excipient or a diluting agent therefor. Preferred pharmaceutical composition is a sustained release composition for local administration, which contains a PDE4 inhibitor(s) and a biocompatible and biodegradable polymer(s). It is further preferred that said composition for local administration is in the form of microsphere, which microsphere can be formulated as an injectable preparation.

Examples of PDE4 inhibitor usable as an active ingredient of pharmaceutical compositions of the present invention include all the compounds having PDE4 inhibitory activity, for example, those described in JP 05-229987A (1993), JP 09-59255A (1997), JP 10-226685A (1998), EP 158380, WO/94/25437, U.S. Pat. No. 5,223,504, WO/95/4045, EP 497564, EP 569414, EP 623607, EP 163965, U.S. Pat. No. 5,605,914, WO/95/35282, WO/96/215, U.S. Pat. Nos. 5,804,588, 5,552,438, WO/93/9118, WO/96/31485, EP 459505, WO/97/22585, EP 738715, WO/91/16314, WO/96/218, WO/97/18208, EP 158380, WO/99/50270, EP 260817, WO/98/11113, WO/94/22852, EP 432856, U.S. Pat. No. 4,193,926, WO/98/13348, WO/96/6843, JP 2000-503678A (WO/98/14432), JP 2000-502724A (WO/98/9961), JP 2000-510105A (WO/97/40032), JP 2000-514804A (WO/98/2440), JP 2000-502350A (WO/97/23457), JP 2000-501741A (WO/97/2585), and the like.

PDE can be classified into PDE1-5 according to the teaching of "Trends in Pharmacological Sciences, vol. 11, pp. 150-155", and PDE4 inhibitors suitable for the present bone fracture healing accelerating composition are preferably selective to PDE4 with higher inhibitory activity against PDE4 compared to others (PDE1-3, 5), more preferably have 10 times or more inhibitory activity on PDE4 than on the other PDEs. The inhibitory activity of such PDE4 inhibitor on PDE4 is particularly preferably 50 times or more, and yet more preferably 100 times or more of that on the other PDEs.

Preferable PDE4 inhibitors are compounds of which $IC_{50}$ of PDE4 inhibitory activity is 0.1-100 nM, preferably 0.1-100 nM, more preferably less than 100 nM, when determined by a method described in "Advances in Cyclic Nucleotide Research", vol. 10, pp. 69-92, 1979, Raven Press.

Specific examples of selective PDE4 inhibitors include Compounds (1) to (57) represented by the following formulas or pharmaceutically acceptable salts thereof.

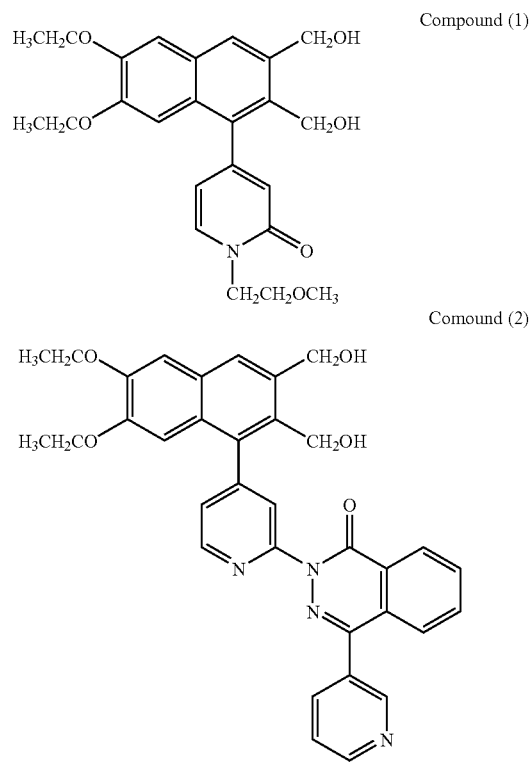

Compound (1)

Comound (2)

-continued
Compound (3)
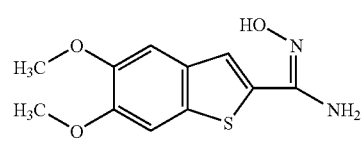
Compound (4)
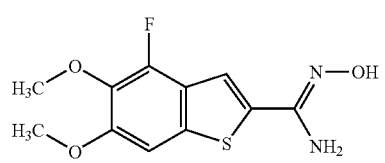
Compound (5)
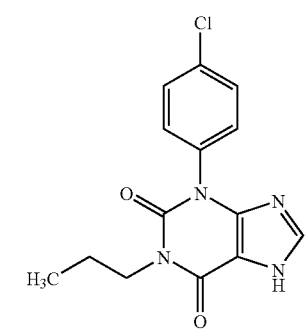
Compound (6)
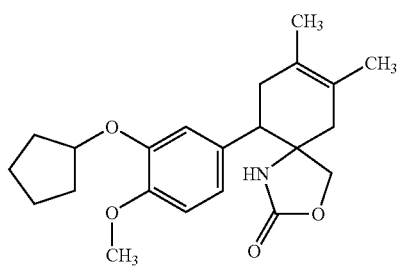
Compound (7)
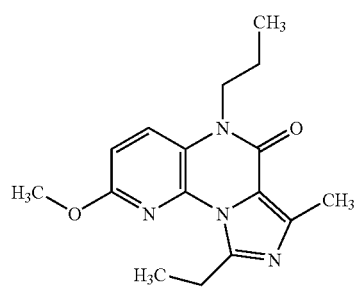
Compound (8)
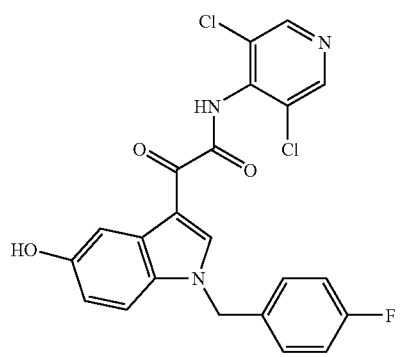
-continued
Compound (9)
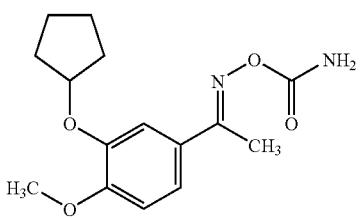
Compound (10)
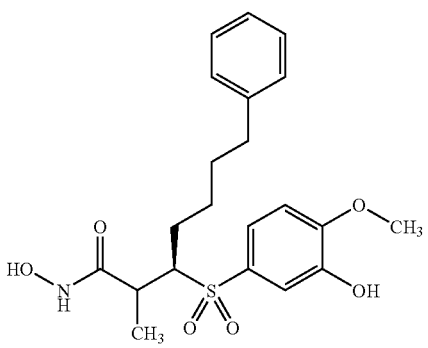
Compound (11)
Compound (12)
Compound (13)
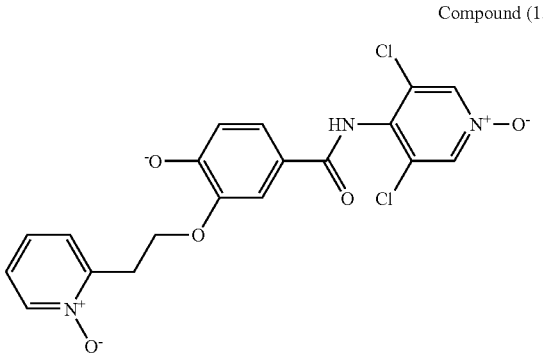

-continued
Compound (14)
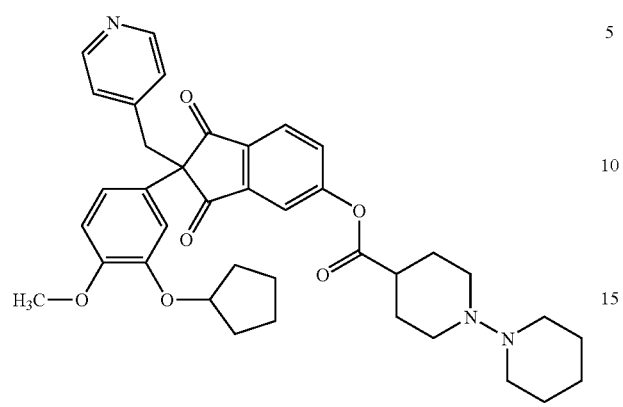
Compound (15)
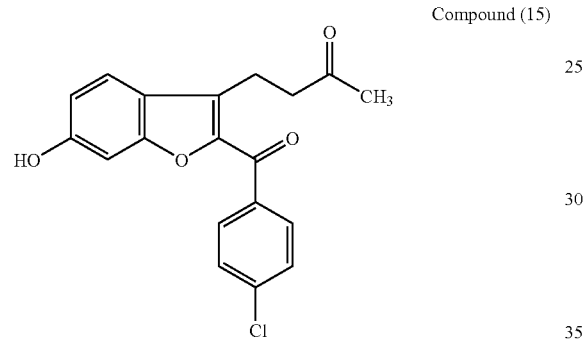
Compound (16)
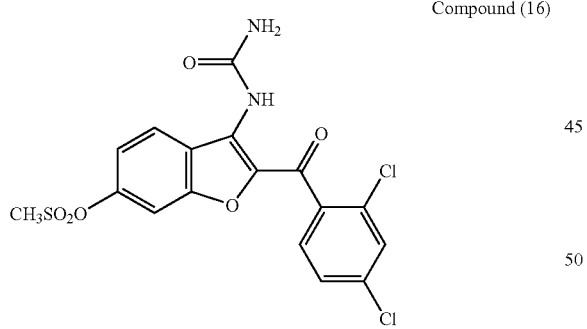
Compound (17)
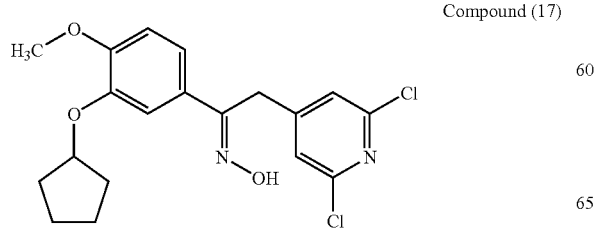
-continued
Compound (18)
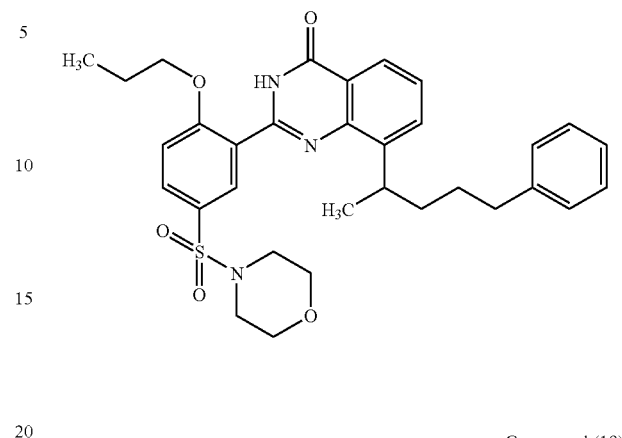
Compound (19)
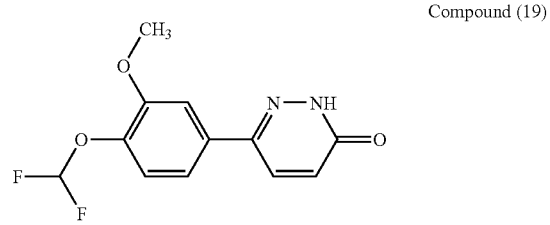
Compound (20)
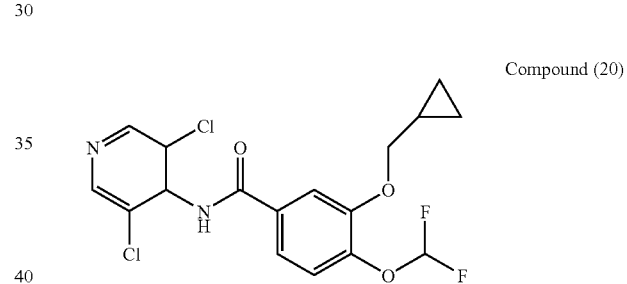
Compound (21)
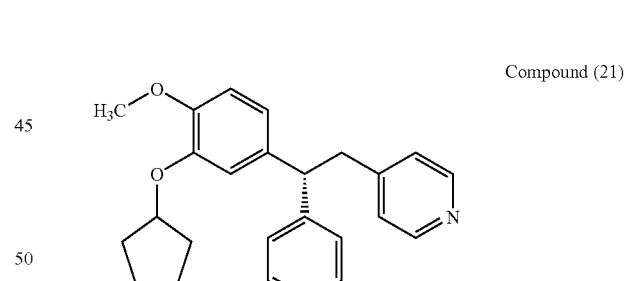
Compound (22)
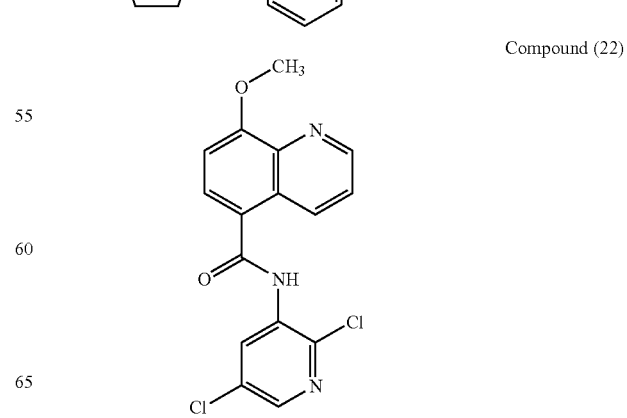

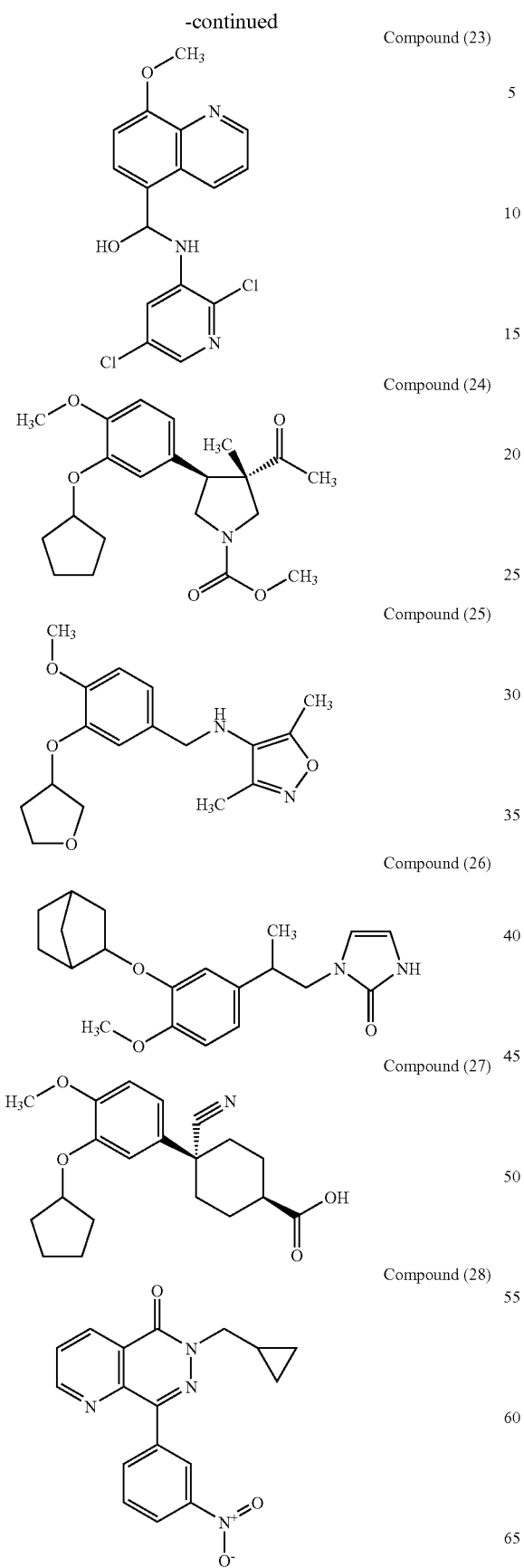

-continued
Compound (34)
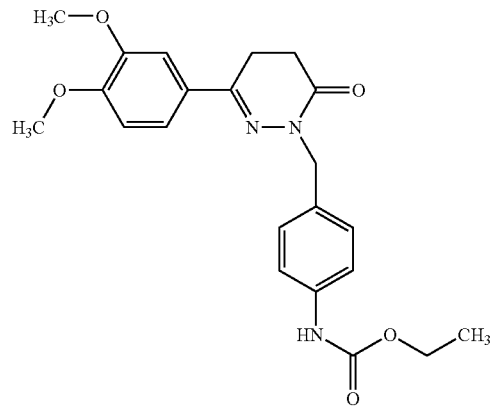
Compound (35)
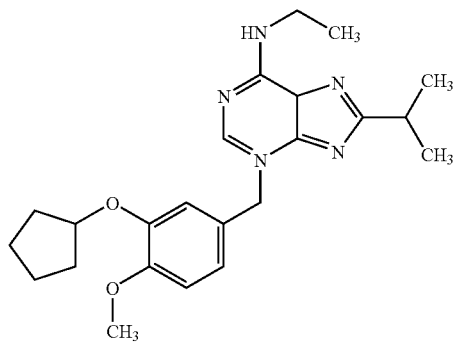
Compound (36)
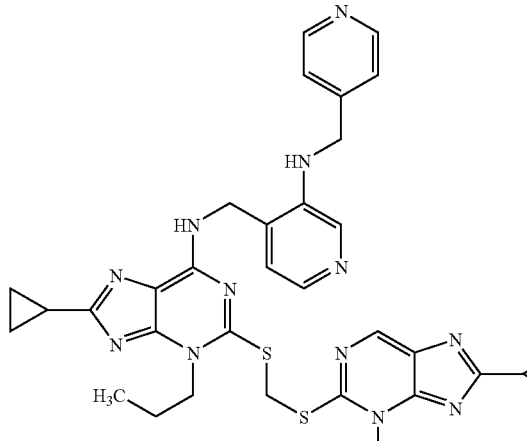
Compound (37)
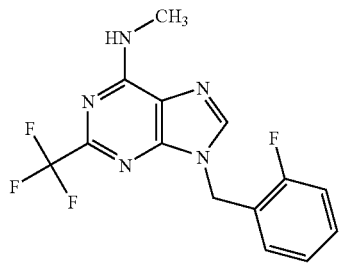
-continued
Compound (38)
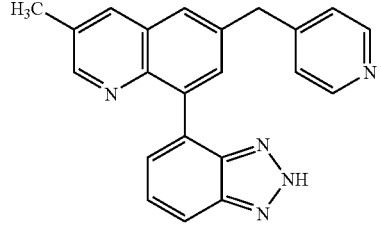
Compound (39)
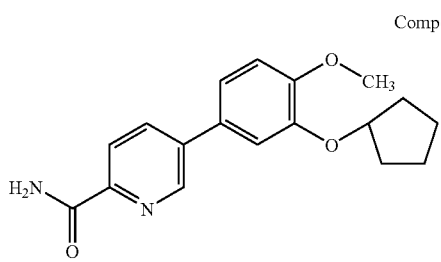
Compound (40)
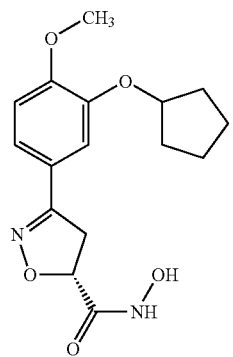
Compound (41)
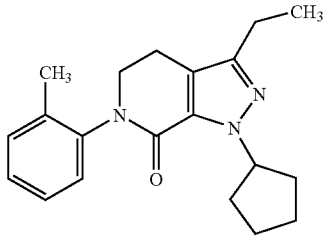
Compound (42)
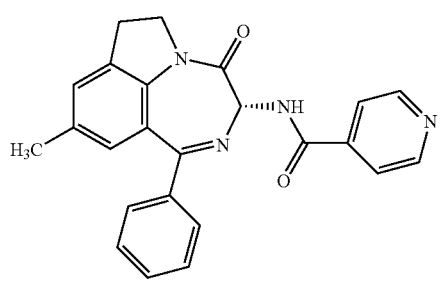

Compound (43)
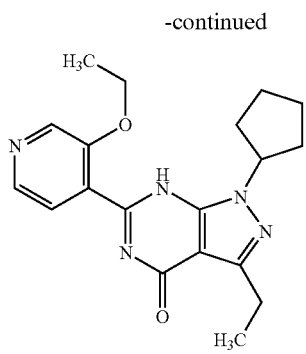
Compound (44)
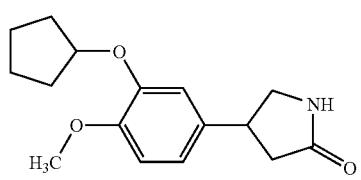
Compound (45)
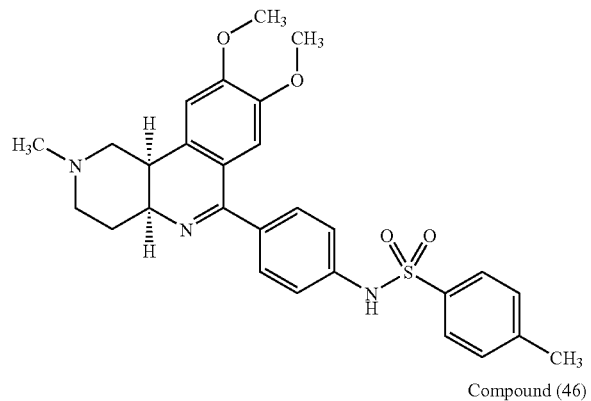
Compound (46)
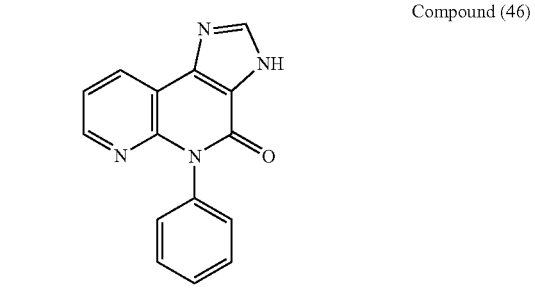
Compound (47)
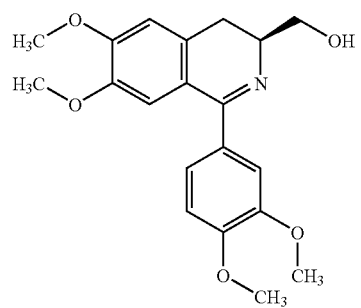
Compound (48)
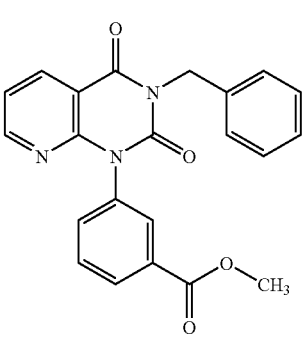
Compound (49)
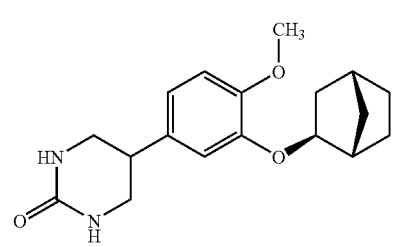
Compound (50)
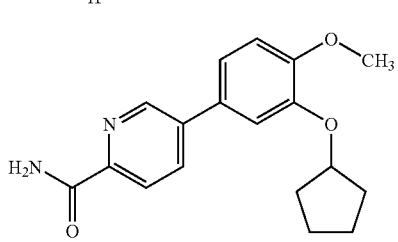
Compound (51)
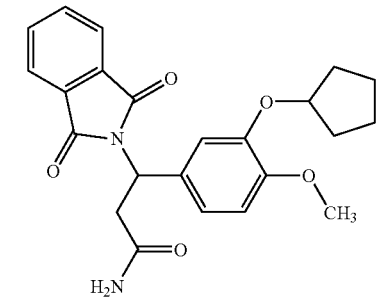
Compound (52)
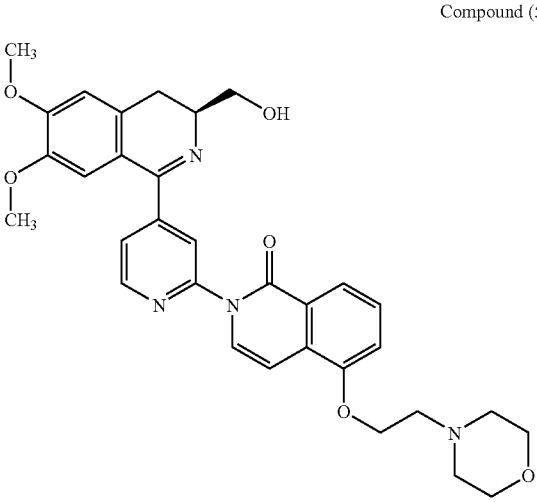

Compound (53)
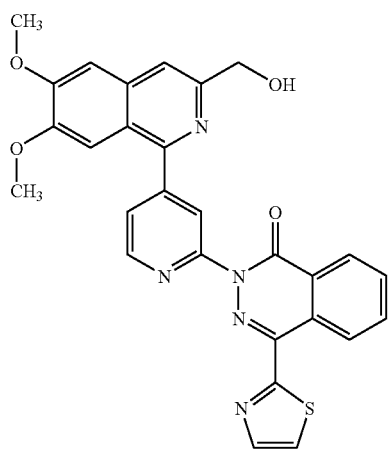

Compound (56)
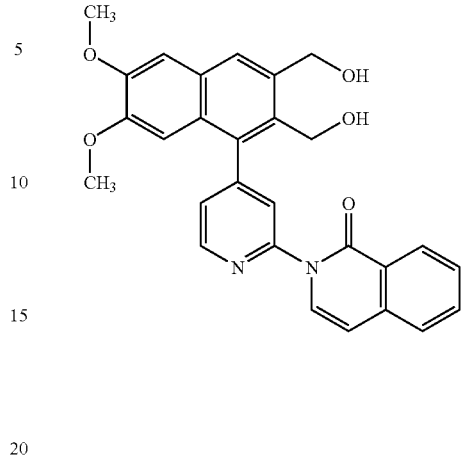

Compound (54)
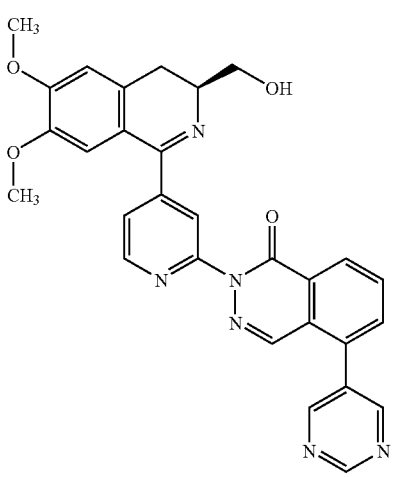

Compound (57)
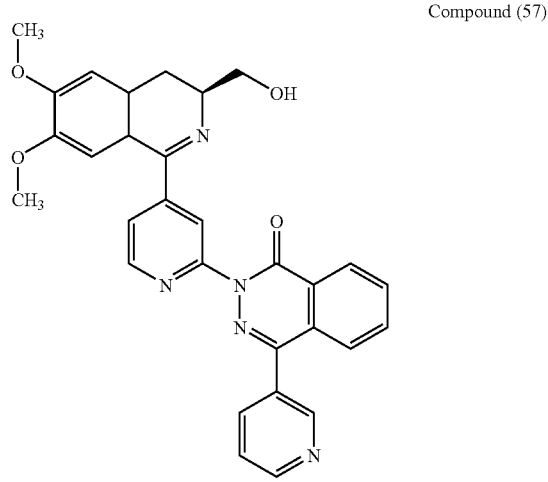

Compound (55)
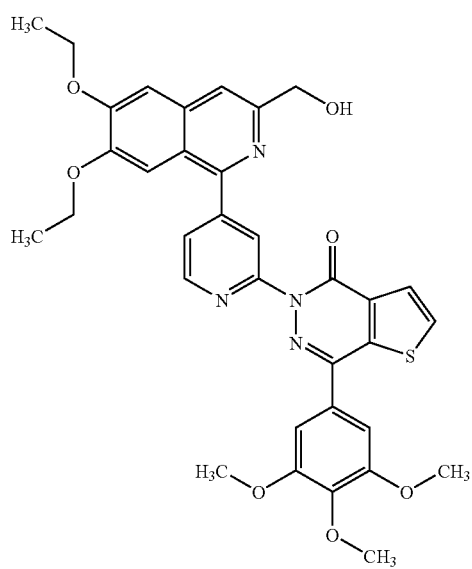

The compounds having PDE4 inhibitory activity can be classified into (A) to (D) below according to the chemical structure, and a PDE4 inhibitor for the present invention can be selected from these compounds appropriately; however, preferred compounds belong to (A) and (B), in particular, (A).

(A) Compounds having naphthalene skeleton or a partial structure analogous thereto [e.g., Compounds (1), (2), (38), (47), and (52) to (57)];

(B) Compounds having 3-cyclopentyloxy-4-methoxyphenyl structure or a partial structure analogous thereto [e.g., Compounds (6), (9), (11), (12), (14), (17), (19), (20), (21), (24), (25), (26), (27), (33), (34), (35), (39), (40), (44), (49), (50) and (51)];

(C) Compounds having a xanthine skeleton or a partial structure analogous thereto [e.g., Compounds (5), (7), (28), (29), (30), (31), (32), (36), (37), (41), (43) and (46)]; and (D) Compounds having a different structure from those described in (A) to (C) above [e.g., Compounds (3), (4), (8), (10), (13), (15), (16), (18), (22), (23), (42), (45) and (48)].

Examples of compounds of group (A) include those shown by the following formulas (I) to (III) and pharmacologically acceptable salts thereof.

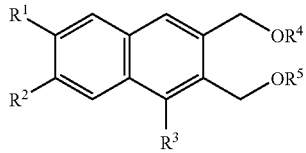
(I)

Wherein $R^1$ and $R^2$ are the same or different and each a hydrogen atom, a hydroxyl group, a cyclo-lower alkyloxy group, or an optionally substituted lower alkoxy group, or bind together at the ends to form a lower alkylenedioxy group;
$R^3$ is an optionally substituted 6-membered nitrogen-containing heterocyclic group; and
—$OR^4$ and —$OR^5$ are the same or different and each an optionally protected hydroxyl group. JP 05-229987A, (1993).

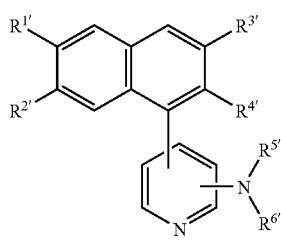
(II)

Wherein $R^{1\prime}$ and $R^{2\prime}$ are the same or different and each a hydrogen atom or an optionally protected hydroxyl group; either of $R^3$ and $R^4$ is an optionally protected hydroxy-substituted methyl group and the other is a hydrogen atom, a lower alkyl group or an optionally protected hydroxy-substituted methyl group; and
$R^{5\prime}$ and $R^{6\prime}$ are the same or different and each a hydrogen atom, an optionally substituted lower alkyl group, an optionally substituted phenyl group or an optionally protected amino group, or bind together at the ends and form in association with the adjacent nitrogen atom an optionally substituted heterocyclic group. JP-09-59255A, (1993).

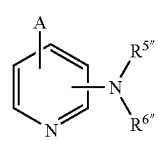
(III)

Wherein A is a group selected from those shown by the formulas:

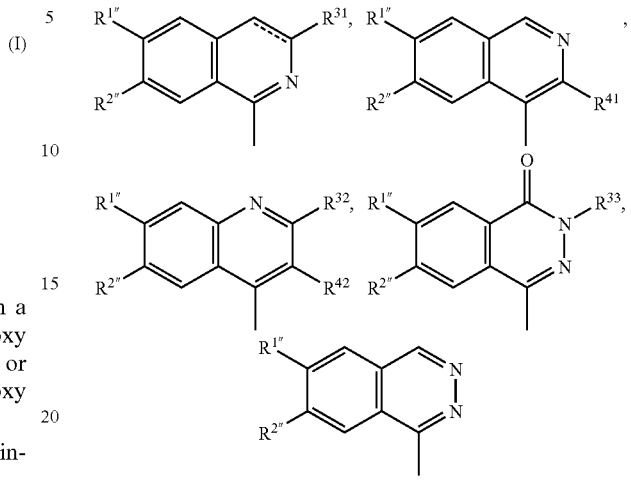

wherein $R^{1\prime}$ and $R^{2\prime}$ are the same or different and each a hydrogen atom or an optionally protected hydroxyl group; $R^{31}$ is an optionally protected hydroxymethyl group; $R^{32}$ is a hydrogen atom, a lower alkyl group or an optionally protected hydroxymethyl group; $R^{33}$ is an optionally substituted lower alkyl group; $R^{41}$ is an optionally protected hydroxymethyl group; $R^{42}$ is an optionally protected hydroxymethyl group; the dotted line represents the presence or absence of a double bond; and
$R^{5\prime}$ and $R^{6\prime}$ are the same or different and each a hydrogen atom or an optionally protected amino group, or bind together at the ends and form in association with the adjacent nitrogen atom an optionally substituted heterocyclic group. JP-10-226685A, (1998).

As a PDE4 inhibitor which is an active ingredient of the present bone fracture healing accelerating composition, among group (A), compounds having naphthalene or isoquinoline skeleton and pharmaceutically acceptable salts thereof are more preferred, and Compounds (1) and (2) and their pharmaceutically acceptable salts are still more preferred.

Since PDE4 inhibitors may cause vomiting or gastric acid secretion depending on dosage when acted systemically (Cellular Signaling, 9 (3-4), pp. 227-236 (1997)), the bone fracture healing accelerating composition of the present invention is preferably applied locally to a vicinity of fracture region so that the drug concentration in the systemic blood does not increase but the one at the fracture region is maintained. To establish this purpose, it is preferred to formulate the composition into a sustained release form, which can advantageously reduce the frequency of administration and also decrease the burden of patients.

Examples of preferred embodiments of the present composition include depot preparations which gradually release a drug when administered locally (e.g., pellet preparation, gel preparation, matrix preparation, microsphere preparation, a sustained release preparation obtained by adding a drug into an aqueous solution of a biocompatible and biodegradable polymer, a preparation which is designed to be a liquid at the time of administration and to form a gel in a living body after administration, a preparation embedded in various bases which are reported to be generally used in the field of orthopedics, and the like.)

Examples of pellet preparations include a long-term sustained release preparation obtainable by compressing a drug and fine particles of lactic acid-glycolic acid copolymer of which terminal carboxyl group is esterified by an alcohol, and the like. (JP2001-187749A)

Examples of gel preparations include those obtained by dissolving into a phosphate buffer a drug and hyaluronic acid which is chemically bound to polyethylene glycol (Journal of Controlled Release, 59 (1999) pp. 77-86), and the like.

Examples of matrix preparations comprising a drug include those obtained by impregnating a drug into granular material of collagen or fibrous membrane preparation, or by adding a drug to a granular material of collagen or a reaction mixture for preparing a fibrous membrane preparation, and the like (JP10-182499A (1998), JP06-305983 (1994)).

Examples of a sustained release preparation obtained by adding a drug into an aqueous solution of a biocompatible and biodegradable polymer include those obtained by adding a drug into an aqueous sodium hyaluronate solution, and the like.

Examples of a preparation designed to be a liquid at the time of administration and to form a gel in a living body after administration include those wherein a drug and a lactic acid-glycolic acid copolymer are dissolved in N-methyl-2-pyrrolidone (Journal of Controlled Release, 33 (1995) pp. 237-243), or a preparation comprising a drug and a polymer that exists as an solution at low temperature but forms a gel at body temperature, such as a block co-polymer of lactic acid-glycolic acid copolymer and polyethylene glycol and the like (ibid., 27 (1993), 139-147).

Examples of a preparation embedded in various bases which are reported to be generally used in the field of orthopaedics include those prepared by mixing a drug and a base (e.g., water-insoluble biocompatible and biodegradable polymer, polymethyl methacrylate, hydroxyapatite, tricalcium phosphate or the like). Biomaterials, vol. 21, pp. 2405-2412 (2000); and International Journal of Pharmaceutics, vol. 206, pp. 1-12 (2000).

Preparations for local administration that release an effective amount of PDE4 inhibitor gradually in affected fracture region are preferred in the respect that the administration frequency during the term required for bone fracture healing can be reduced.

Among depot preparations, in the case of microspheres feasible for local administration by injection, the particle size of such microspheres is preferably in the range suitable for passing a needle, more preferably 0.01-150 µm, particularly preferably 0.1-100 µm in the respect that the irritation at the affection site can be reduced.

Since the present bone fracture healing accelerating composition containing a PDE4 inhibitor as an active ingredient is administered locally to a vicinity of fracture region, it would be preferable to make the dosage small. Accordingly, the PDE4 inhibitor content in the composition such as microsphere preparation can be preferably 0.0001-80% by weight, more preferably 0.001-50% by weight, and further more preferably 0.01-50% by weight.

The dose of a PDE4 inhibitor as an active ingredient may vary depending on the kind of PDE4 inhibitor to be used, the weight, age, conditions of the subject or a site to be applied and is generally determined by a physician; however, for local administration, the dose can usually be in the range of from 1 ng to 1 g per affected site.

The bone fracture healing accelerating composition of the present invention can be prepared in a conventional manner using a PDE4 inhibitor and a pharmaceutically acceptable excipient or a carrier therefor. Preferred composition can be prepared by combining a PDE4 inhibitor and a biocompatible and biodegradable polymer.

Among them, the water-insoluble biocompatible and biodegradable polymer is a water-insoluble biocompatible and biodegradable polymer that requires at least 1000 ml of water to dissolve 1 g of the polymer at 25° C., and specific example include hydroxy fatty acid polyesters and derivatives thereof (for example, poly lactic acid, poly glycolic acid, poly citric acid, poly malic acid, poly-β-hydroxybutyric acid, ring-opening polymerized ε-caprolactones, lactic acid-glycolic acid copolymer, 2-hydroxybutyric acid-glycolic acid copolymer, block copolymer of poly lactic acid and polyethylene glycol, block copolymer of poly glycolic acid and polyethylene glycol, and block copolymer of lactic acid-glycolic acid copolymer and polyethylene glycol, etc.), polymers of alkyl α-cyanoacrylates (e.g., polybutyl-2-cyanoacrylate, etc.), polyalkylene oxalate (e.g., polytrimethylene oxalate, polytetramethylene oxalate, etc.), polyortho-esters, polycarbonates (e.g., polyethylene carbonate, polyethylenepropylene carbonate, etc.), polyortho-carbonates, polyamino acids (e.g., poly-γ-L-alanine, poly-γ-benzyl-L-glutamic acid, poly-γ-methyl-L-glutamic acid, etc.), hyaluronic acid esters. One or more of these polymers can be used. Other biocompatible and biodegradable polymers include sodium hyaluronate, chondroitin sulfate, collagen, gelatin, fibrin, and the like.

Among the water insoluble biocompatible and biodegradable polymers above, hydroxy fatty acid polyesters are particularly preferred. Above all, those of which average molecular weight ranging in between 2000 and about 800000 are more preferred, those ranging in between 2000 and about 200000 are especially preferred and those ranging in between 5000 and 50000 are most preferred.

In addition, among the hydroxy fatty acid polyesters above, poly lactic acid, lactic acid-glycolic acid copolymer and 2-hydroxybutyric acid-glycolic acid copolymer are more preferred. The molar ratio of lactic acid and glycolic acid in a lactic acid-glycolic acid copolymer is preferably 90:10 to 30:70, more preferably 80:20 to 40:60, and the molar ratio of 2-hydroxybutyric acid and glycolic acid in a 2-hydroxybutyric acid-glycolic acid copolymer is preferably 90:10 to 30:70, more preferably 80:20 to 40:60.

When formulating a PDE4 inhibitor above into a depot preparation, it can be carried out appropriately depending on the intended embodiment, optionally after pulverizing a PDE4 inhibitor if necessary.

Pulverization of PDE4 inhibitor can be carried out using any one of conventional methods for producing fine particles including mechanical pulverization methods such as jet mill, hammer mill, convolution ball mill, jar ball mill, beads mill, shaker mill, rod mill and tube mill pulverizations, or so-called crystallization method wherein a drug is first dissolved in a solvent and then recrystallized by adjusting pH, changing temperature, or altering the constitution of solvent, and recovering the particles by centrifugation, filtration, or the like.

When preparing the above-mentioned various types of formulations of the present pharmaceutical composition, any appropriate process can be used depending on the selected PDE4 inhibitor.

For example, microsphere preparation can be prepared by the following methods. In case that a salt of a PDE4 inhibitor shows low incorporation rate into a microsphere, it may be converted into corresponding free form using an acid or a base prior to the preparation of microspheres.

(1) In-Water Drying Method

In this method, a drug is added to a solution of water-insoluble biocompatible and biodegradable polymer in a water-immiscible organic solvent of which boiling point is lower than water (water-insoluble polymer solution), and the resultant organic phase is dispersed into an aqueous phase to give an o/W emulsion, which is followed by removal of the organic solvent. This method can be conducted in a manner similar to those described in, for example, JP 56-19324B (1981), JP 63-91325A (1988), JP 08-151321A (1996), Kajeev Jain et al., "Controlled Drug Delivery by Biodegradable Poly (Ester) Devices: Different Preparative Approaches", Drug Development and Industrial Pharmacy, vol. 24(8), pp. 703-727, 1998, JP 60-100516A (1985), JP 62-201816A (1987), JP 09-221417A (1997) and JP 06-211648A (1994).

(2) Phase Separation Method

In this method, into a solution of water-insoluble biocompatible and biodegradable polymer in an organic solvent is dissolved or dispersed a drug, or is dispersed an aqueous solution of the drug. A hardening agent is then added gradually with stirring to obtain solid precipitations. This method can be conducted in a manner similar to those described in, for example, JP 60-67417A (1985), U.S. Pat. Nos. 5,503,851, 5,000,886, Eur. J. Pharm. Biopharm. vol. 42 (1), pp. 16-24 (1996) and the forecited Jain et al. (ibid.)

(3) Spray Drying Method

In this method, to a solution of water insoluble biocompatible and biodegradable polymer in an organic solvent is dissolved or dispersed a drug, or is dispersed an aqueous solution of the drug. The resultant solution or dispersion is then sprayed via a nozzle into a drying chamber of a spray drier to volatilize the organic solvent in the fine droplets in a very short time. This method can be conducted in a manner similar to those described in, for example, JP 01-155942A (1989), JP 05-194200A (1993), JP 05-70363A (1993), JP 08-151321A (1996), JP 09-221417A (1997), U.S. Pat. No. 5,922,253, "Spray Drying Handbook" (John Wiley & Sons, New York 1984), Partick B. Deasy, "Microcapsulation and Related Drug Processes" (Marcel Dekker, Inc., New York 1984) and the forecited Jain et al. (ibid), and the like.

(4) Solvent Diffusion Method

In this method, a solution of a drug and a water insoluble biocompatible and biodegradable polymer in a water miscible organic solvent is added to an aqueous solution of protective colloid, followed by emulsification with stirring to yield fine particles. This method can be conducted in a manner similar to those described in, for example, JP 05-58882A (1993), JP 09-110678A (1997) and International Journal of Pharmaceutics, vol. 187, pp. 143-152 (1999).

In the aforementioned "In-Water Drying Method", different preparation processes may be employed depending on the type of organic phase though they all can be conducted in a conventional manner. Examples of organic phase include the followings.

(a) An organic phase wherein a drug is directly dissolved or dispersed in a solution of a water-insoluble, biocompatible and biodegradable polymer. This, when dispersed in an aqueous phase, gives O/W emulsion (JP 56-19324B (1981), JP 63-91325A (1988), JP 06-32732A (1994), JP 08-151321A (1996), JP 06-32732A (1994), and the forecited Jain, etc.)

(b) An organic phase which is W/o emulsion wherein an aqueous solution of a drug is dispersed in a solution of a water-insoluble, biocompatible and biodegradable polymer. The W/O emulsion, when dispersed in an aqueous phase, gives (W/O)/W emulsion (JP 60-100516A (1985), JP 62-201816A (1987), JP 09-221417A (1997), and the forecited Jain, etc.)

(c) An organic phase which is O/O emulsion, which uses two or more water-insoluble, biocompatible and biodegradable polymers, wherein a drug is dissolved or dispersed in a polymer solution that is dispersed in the other(s). The O/O emulsion, when dispersed in an aqueous phase, gives (O/O)/W emulsion (JP 06-211648A (1994)).

By using any of the organic phases above, the emulsification can be achieved by a conventional method, for example, the intermittent shaking method, the method using a mixer such as a propeller shaker or a turbine shaker, the colloidal mill method, the homogenizer method and the ultrasonication method.

Examples of organic solvent usable in these methods include halogenated hydrocarbons (methylene chloride, chloroform, carbon tetrachloride, chloroethane, dichloroethane, trichloroethane, etc.), aliphatic esters (ethyl acetate, butyl acetate, etc.), aromatic hydrocarbons (benzene, etc.), aliphatic hydrocarbons (n-hexane, n-pentane, cyclohexane, etc.), ketones (methylethyl ketone, etc.), ethers (diethyl ether, diisopropyl ether, methyl isobutyl ether, etc.)

In preparation of emulsion above, an emulsifier may be added to an aqueous phase to stabilize emulsion, which emulsifier includes, for example, anionic surfactants (sodium oleate, sodium stearate, sodium lauryl sulfate, etc.), nonionic surfactants {polyoxyethylene sorbitan fatty acid ester [Tween80, Tween 60 (Nikko Chemicals, Co., Ltd.)], polyethylene castor oil derivatives [HCO-60, HCO-50 (Nikko Chemicals, Co., Ltd.)], polyvinylpyrrolidone, polyvinyl alcohol, carboxymethyl cellulose, methyl cellulose, lecithin, gelatin, etc.

Further, when one or more other ingredients are incorporated in addition to PDE4 inhibitor, the former can be preferably added to the organic phase at the time of preparation of O/W emulsion. To obtain a microsphere preparation with an elevated concentration of medicinal ingredient, it is necessary to prepare an organic phase containing an active ingredient at high concentration. For this purpose, an osmoregulatory agent may be included in an aqueous phase to prevent the outflow of an active ingredient into an aqueous phase (JP 2608245).

The O/W emulsion obtained in the above-mentioned manner is then subjected to in-water-drying to remove organic solvent present in emulsion to give microspheres.

Organic solvent can be removed from emulsion in a conventional manner such as heating, placing under reduced pressure, blowing air, or the like, and for example, a method where a solvent is distilled off in an open system (JP 56-19324B (1981), JP 63-91325A (1988), JP 08-151321A (1996), JP 06-211648A (1994)) or in a closed system (JP 09-221418A (1997)) can be employed. In addition, a method where a solvent is extracted and removed by means of a large quantity of outside water phase (JP-2582186) can also be used.

Further, the following methods can be appropriately used depending on the PDE4 inhibitor.

A method wherein a solution containing a drug, a biodegradable polymer and a water-miscible good solvent (Solvent A: acetone, tetrahydrofuran, etc.) for the said polymer is first added to a homogeneous mixed solution comprising a poor solvent (Solvent B: water, ethanol, etc.) for the said polymer, which is miscible with solvent A, and a poor solvent (Solvent C: glycerin, etc.) for the said polymer, which is immiscible with solvent A. The mixture, upon emulsification, gives emulsion wherein the polymer solution constitutes the dispersed-phase and the homogeneous mixed solution constitutes the continuous-phase. The solvent A is then removed from the dispersed phase (WO/01/80835).

A method for preparing microspheres from emulsion by in-water-drying method, in which emulsion an organic phase containing an organic solvent with a boiling point lower than water (methylene chloride, ethyl acetate, etc.) and a water insoluble polymer is emulsified in an aqueous phase, comprising (1) employing a device equipped with a gas separation membrane (permeable evaporation membrane, porous membrane, etc.), (2) providing emulsion to be subjected to the in-water-drying to one side of the gas separating membrane, and (3) distilling off the organic solvent in emulsion to the other side of the gas separating membrane (WO/01/83594).

Furthermore, the organic solvent remaining in microspheres can be removed by heating microspheres in an aqueous phase at temperature higher than the boiling point of the organic solvent (JP 2000-239152A) or heating the microspheres to dry after coating with an additive of high melting point (JP 09-221417A (1997)).

The resultant microspheres are recovered by centrifugation, filtration or sieving, washed to remove substances attached on the surface such as additives in the water-phase, and subjected to lyophilization optionally after combining with an aggregation inhibitor to prevent the agglomeration of microspheres, for example, sugar, sugar alcohol or inorganic salt, preferably lactose, mannitol or sorbitol. It is preferred to use a sieve to obtain microspheres of an intended particle size, and it is more preferred to use a sieve allowing particles of, for example, 150 μm or below to pass so as to improve the syringeability when the microsphere preparation is used as injectable solution.

For preparing microspheres by "Phase Separation Method", amphiphilic solvents such as acetone, acetonitrile, tetrahydrofuran and dioxane in addition to the organic solvents used in the "In-water Drying Method" above can be used. A PDE4 inhibitor and optionally one or more additional ingredients, or a solution thereof, are dissolved or dispersed in an organic solution of water insoluble polymer in any one of these organic solvents to form an organic phase. The organic phase is added gradually to a solvent (disperse medium) immiscible with the organic solvent above, for example, silicon oil, liquid paraffin, sesame oil, soybean oil, corn oil, cotton seed oil, coconuts oil, linseed oil, with stirring to form O/O emulsion. If desired, a surfactant may be added to the disperse medium. The water insoluble polymer can be solidified by cooling the emulsion or evaporating the solvent in the organic phase by heating. Alternatively, a hardening agent such as hexane, cyclohexane, methyl ethyl ketone, octamethyl-cyclotetrasiloxane or the like can be added gently to emulsion with stirring, or versa, to separate out the water insoluble polymer from emulsion thereby forming microspheres.

The resultant microspheres are recovered by centrifugation, filtration or sieving, washed with hexane or purified water to remove solvents, additives, etc. attached on its surface, and optionally subjected to air-drying, vacuum-drying, or lyophilization. Alternatively, it can be lyophilized after adding an aggregation inhibitor in a manner similar to that used in the above-mentioned in-water-drying method.

Examples of internal organic phase in the phase separation method include the following embodiments.

(a) An organic phase wherein a drug is directly dissolved or dispersed in a solution of a water-insoluble, biocompatible and biodegradable polymer.

(b) An organic phase which is W/o emulsion wherein an aqueous solution of a drug is dispersed in a solution of a water-insoluble, biocompatible and biodegradable polymer.

(c) An organic phase which is O/O emulsion, which uses two or more water-insoluble, biocompatible and biodegradable polymers, wherein a drug or a solution thereof is dissolved or dispersed in a polymer solution that is dispersed in the other(s).

Further, the preparation of microspheres by "Spray Drying Method" is conducted using the same organic solvent as the above-mentioned phase separation method. To an organic solvent is dissolved a water insoluble biocompatible and biodegradable polymer, and a PDE4 inhibitor and optionally one or more additional ingredients, or a solution thereof, are dissolved or dispersed in the solution, and sprayed via a nozzle into a drying chamber of a spray drier to volatilize the organic solvent to form microspheres.

For the present invention, any commercially available spray dryers, for example, such as Pulvis Mini Spray GS31 (YAMATO Scientific Co., Ltd.), Mini Spray Dryer (Shibata Scientific Technology, Co., Ltd.), can be used.

The resultant microspheres are then worked-up in a manner similar to that used in the in-water drying method to yield the desired microsphere preparation.

Examples of water-miscible organic solvents usable in the "Solvent Diffusion Method, include acetone, methanol, ethanol or a mixture thereof, which may further contain a volatile solvent (methylene chloride, chloroform) in which a drug can dissolve, if necessary. Examples of colloid protective agent include polyvinyl alcohol.

When the microsphere preparation of the present composition for accelerating the bone fracture healing comprising a PDE4 inhibitor as an active ingredient is administered to a vicinity of fracture region, it can be preferably applied locally, more preferably, as injection or implant.

An injectable preparation of microspheres can be prepared by dispersing/suspending microspheres obtained by the present invention at a concentration of 0.0001-1000 mg/ml, preferably 0.0005-800 mg/ml, more preferably 0.001-500 mg/ml into an aqueous solution containing a dispersant.

Examples of dispersant include nonionic surfactants such as polyoxyethylene sorbitan fatty acid ester (Tween80, Tween60, Nikko Chemicals Co., Ltd.), polyethylene castor oil (HCO-60, HCO-50, Nikko Chemicals Co., Ltd.), cellulose-derived dispersants such as carboxymethyl cellulose sodium, sodium alginate, dextran, sodium hyaluronate, and the like. These dispersants can serve to improve the dispersibility of microspheres and stabilize the elution of an active ingredient. A dispersant can generally be added to a composition at a concentration of 0.01-2% by weight, preferably 0.05-1% by weight.

The injectable preparation above may optionally contain a preservative (methylparaben, propylparaben, benzyl alcohol, chlorobutanol, sorbic acid, boric acid, amino acid, polyethylene glycol, etc.), an isotonizing agent (sodium chloride, glycerin, sorbitol, glucose, mannitol, etc.), a pH modifier (sodium hydroxide, potassium hydroxide, hydrochloric acid, phosphoric acid, citric acid, oxalic acid, carbonic acid, acetic acid, arginine, lysine, etc.), a buffer (sodium hydrogen phosphate, potassium hydrogen phosphate, etc.) or the like.

If necessary, a steroid antiinflammatory analgesic or non-steroidal antiinflammatory analgesic may be dissolved or dispersed in the injectable preparation. Examples of steroidal antiinflammatory analgesic include dexamethasone, triamcinolone, triamcinolone acetonide, halopredone, parametha-sone, hydrocortisone, prednisolone, methylprednisolone, betamethasone, and the like. Examples of non-steroidal antiinflammatory analgesic include ibuprofen, ketoprofen, indomethacin, naproxen, piroxicam, and the like.

In addition to the above-mentioned suspension, the microsphere injection containing PDE4 inhibitor can be in the form of a kit for preparing an injectable preparation at the time of use, which kit comprises a solid preparation of an aggregation inhibitor and microspheres, a dispersant and injectable distilled water.

The solid preparation used in a kit can be prepared by suspending microspheres in an aqueous solution containing an aggregation inhibitor, and subjecting the suspension to lyophilization, vacuum drying, or spray drying, and/or the like. The lyophilization is especially preferred.

When preparing a solid preparation, a dispersant can be added to an aqueous solution containing aggregation inhibitor (mannitol, sorbitol, lactose, glucose, xylitol, maltose, galactose, sucrose, etc.) in order to improve the re-dispersibility into injectable distilled water, thereby yielding a solid preparation of good dispersibility. If necessary, it can be formulated into a kit for preparing an injectable preparation, in which a steroidal antiinflammatory analgesic and/or a nonsteroidal antiinflammatory analgesic as well as a dispersant are combined.

The present bone fracture healing accelerating composition comprising a PDE4 inhibitor as an active ingredient can be used in treatment of various warm blood mammals such as human, a domestic animal (a horse, a bull, a sheep, a pig), a pet (a dog, a cat), and the like.

Examples of disorders to which the present fracture healing accelerating composition comprising a PDE4 inhibitor as an active ingredient applicable include (a) fracture by external force, (b) pathological fracture (fracture associated with osteoporosis, osteomalacia, malignant tumor, multiple myeloma, osteogenesis imperfecta congenita, cyctic bone, suppurative myelitis, osteopetrosis or nutrition disorders), and (c) fatigue fracture. In addition, the present fracture healing accelerating composition comprising a PDE4 inhibitor as an active ingredient can be applied to any of the following fractures, including fissure fracture, greenstick fracture, transverse fracture, oblique fracture, spiral fracture, segmental fracture, comminuted fracture, avulsion fracture, compression fracture, depression fracture, and the like

EXAMPLES

The following Experimental Examples, Examples and Test Examples are provided to further illustrate the present invention. Throughout the following examples, a compound with a given number is the same compound indicated by the same number in the list above which shows specific examples of preferred compounds with chemical structure.

Experimental Example 1

Acceleration of Fracture Healing in Normal Rat (Acclimation)
CD (SD) IGS rats (Charles River Japan, Inc.; male; 7-week-old) were housed for seven days at room temperature ($23\pm2°$ C.) and 40-70% humidity. During the housing period, the rats were free to access commercially available food (from Oriental Bio; CE-2).

(Fracture Healing)
Under ether anesthesia, the left-lower legs of rats were shaved and sterilized with 70% aqueous ethanol, fibulas were exposed with scissors and cut with nail scissors (Natsume Seisakusyo; B17). The cut sections of the fibula were re-matched with tweezers. For the test groups (20 rats/group), the drug-containing microspheres prepared in Example 2-(1), which contains 0.1 or 0.5 mg of Compound (1), were placed around the cutting site of each rat using spatula followed by suturing with silk thread. For the control group (20 rats/group), the same amount of drug-free microspheres prepared in Control Example 1-(1) were placed around the cutting site using spatula followed by suturing with silk thread. Following the suturing, animals of every group were sterilized with 70% aqueous ethanol. At six weeks after the suturing, under ether anesthesia, 10 rats from each group were sacrificed by laparotomy with bleeding and the fibulas were excised.

(Experimental Results)

(1) Measurements of Fibula Bone Mineral Density and Bone Mineral Content

The fibula excised at 6 weeks after suturing was subjected to DXA bone densitometer (Aloka; DCS-600) to determine bone mineral density and bone mineral content at fracture region (scanning width: 1 mm).

The results of the measurement of bone mineral density and bone mineral content are shown in Table 1 and 2, respectively.

TABLE 1

Fibula Bone Mineral Density ($mg/cm^2$)

| Drug | Drug Content | Bone Mineral Density ($mg/cm^2$) |
|---|---|---|
| Control | 0 | 33.69 ± 0.80 |
| Compound (1) | 0.1 mg | 36.77 ± 1.52 |
| Compound (1) | 0.5 mg | 40.05 ± 1.34 |

TABLE 2

Fibula Bone Mineral Content (mg)

| Drug | Drug Content | Bone Mineral Content (mg) |
|---|---|---|
| Control | 0 | 11.99 ± 0.50 |
| Compound (1) | 0.1 mg | 14.27 ± 0.76 |
| Compound (1) | 0.5 mg | 15.20 ± 0.82 |

As shown in Tables 1 and 2, it is found that, in the groups treated with drug-containing microspheres, the bone mineral density and bone mineral content in the fracture area have increased in a dose-dependent manner.

(2) Measurements of Fibula Volume

The volume of fibula excised 6 weeks after suturing was determined using Plethysmometer (Muromachi Kikai Co., Ltd.; TK-101).

The results of bone volume measurement are shown in Table 3.

TABLE 3

Fibula Volume (μl)

| Drug | Drug Content | Bone volume (μl) |
|---|---|---|
| Control | 0 | 62.7 ± 2.0 |
| Compound (1) | 0.1 mg | 68.1 ± 2.9 |
| Compound (1) | 0.5 mg | 77.2 ± 2.9 |

As shown in Table 3, it is found that, in the groups treated with drug-containing microspheres, the bone volume of fibula have increased in a dose-dependent manner.

(3) Measurements of Fibula Strength

The fibula excised at 6 weeks after suturing was subjected to a three-point bending test with bone strength tester (from Muromachi Kikai Co., Ltd.; TK-252C) to determine bone strength. Briefly, the fibula was supported by two supports apart from each other by 8 mm and the cut section was positioned at the middle of these supports, i.e., 4 mm apart from the respective two supports. Loading (3 mm/minute) from upper direction was kept on the middle point (fracture section) of fibula until fibula begins to fracture. The maximum pressure necessary to break the bone was defined as the breaking force and the total energy spent to break the bone was defined as the breaking energy.

The results of measurement of breaking energy and breaking force are shown in Tables 4 and 5, respectively.

TABLE 4

Breaking Energy (mJ)

| Drug | Drug Content | Breaking Energy (mJ) |
|---|---|---|
| Control | 0 | 2.27 ± 0.14 |
| Compound (1) | 0.1 mg | 4.37 ± 0.71 |
| Compound (1) | 0.5 mg | 6.44 ± 1.06 |

TABLE 5

Breaking Force (N)

| Drug | Drug Content | Breaking force (N) |
|---|---|---|
| Control | 0 | 15.0 ± 0.94 |
| Compound (1) | 0.1 mg | 19.8 ± 2.14 |
| Compound (1) | 0.5 mg | 23.0 ± 1.68 |

As shown in Tables 4 and 5, it is found that, in the groups treated with drug-containing microspheres, the bone strength at fracture region have increased in a dose-dependent manner.

Experimental Example 2

Acceleration of Fracture Healing in Normal Rats (Acclimation)

CD (SD) IGS rats (Charles River Japan, Inc.; male; 7-week-old) were housed for seven days at room temperature (23±2° C.) and 50±20% humidity. During the housing period, the rats were free to access commercially available food (from Oriental Bio; CE-2).

(Fracture Healing)

Under ether anesthesia, the left-lower legs of rats were shaved and sterilized with 70% aqueous ethanol; fibulas were exposed with scissors and cut with nail scissors (Natsume Seisakusyo; B17). The cut sections of the fibula were rematched with tweezers. For the test groups (15 rats/group), the drug-containing microspheres prepared in Example 7, which contains 0.004, 0.02, 0.1 or 0.5 mg of Compound (2), were placed around the cutting site using spatula followed by suturing with silk thread. For the control group (15 rats/group), the same amount of drug-free microspheres prepared in Control Example 2 were placed around the cutting site using spatula followed by suturing with silk thread. Following the suturing, every animal was sterilized with 70% aqueous ethanol. Five rats at two weeks later and 10 rats at four weeks later were taken from each group and sacrificed by laparotomy with bleeding under ether anesthesia and the fibulas were excised.

(Experimental Results)

(1) Measurements of Fibula Bone Mineral Density and Bone Mineral Content

The fibula excised at 2 weeks after suturing was subjected to DXA bone densitometer (from Aloka; DCS-600) to determine bone mineral density and bone mineral content at fracture region (scanning width: 1 mm).

The results of the measurement of bone mineral density and bone mineral content are shown in Tables 6 and 7, respectively.

TABLE 6

Fibula Bone Mineral Density (mg/cm$^2$)

| Drug | Drug Content | Bone Mineral Density (mg/cm$^2$) |
|---|---|---|
| Control | 0 | 40.48 ± 1.36 |
| Compound (2) | 0.004 mg | 46.18 ± 3.18 |
| Compound (2) | 0.02 mg | 50.72 ± 2.68 |
| Compound (2) | 0.1 mg | 56.06 ± 4.19 |
| Compound (2) | 0.5 mg | 52.18 ± 4.36 |

TABLE 7

Fibula Bone Mineral Content (mg)

| Drug | Drug Content | Bone Mineral Content (mg) |
|---|---|---|
| Control | 0 | 13.62 ± 0.78 |
| Compound (2) | 0.004 mg | 15.90 ± 1.88 |
| Compound (2) | 0.02 mg | 19.86 ± 1.75 |
| Compound (2) | 0.1 mg | 23.10 ± 2.72 |
| Compound (2) | 0.5 mg | 23.24 ± 2.97 |

As shown in Tables 6 and 7, it is found that, in the groups treated with drug-containing microsphere, the bone mineral density and bone mineral content in the fracture area have increased in a dose-dependent manner.

(2) Measurements of Fibula Volume

The volume of fibula excised at 2 weeks after suturing was determined using Plethysmometer (Muromachi Kikai Co., Ltd.; TK-101). The results of bone volume measurement are shown in Table 8.

TABLE 8

Fibula Volume (μl)

| Drug | Drug Content | Bone Volume (μl) |
|---|---|---|
| Control | 0 | 79.20 ± 4.87 |
| Compound (2) | 0.004 mg | 85.0 ± 8.14 |
| Compound (2) | 0.02 mg | 97.6 ± 4.99 |
| Compound (2) | 0.1 mg | 121.6 ± 13.76 |
| Compound (2) | 0.5 mg | 132.2 ± 11.72 |

As shown in Table 8, it is found that, in the groups treated with drug-containing microspheres, the bone volume of fibula have increased in a dose-dependent manner.

(3) Measurements of Fibula Strength

The fibula excised at 4 weeks after suturing was subjected to a three-point bending test with bone strength tester (from Muromachi Kikai Co., Ltd.; TK-252C) to determine bone strength. Briefly, the fibula was supported by two supports apart from each other by 8 mm and the cut section was positioned at the middle of these supports, i.e., 4 mm apart from the respective two supports. Loading (3 mm/minute) from upper direction was kept on the middle point (fracture section) of fibula until fibula begins to fracture. The breaking force and the total energy spent to break the bone was defined as the breaking energy.

The results of measurement of breaking energy are shown in Table 9.

TABLE 9

| Drug | Drug Content | Breaking Energy (mJ) |
|---|---|---|
| Control | 0 | 2.19 ± 0.33 |
| Compound (2) | 0.004 mg | 2.66 ± 0.49 |
| Compound (2) | 0.02 mg | 2.59 ± 0.55 |
| Compound (2) | 0.1 mg | 3.15 ± 0.54 |
| Compound (2) | 0.5 mg | 3.27 ± 0.61 |

As shown in Table 9, it is found that, in the groups treated with drug-containing microsphere, the bone strength at fracture region have increased in a dose-dependent manner.

Experimental Example 3

In Vitro Test (Isolation of Costicartilage Cell)

Costicartilages were isolated from NZ line rabbit (Kitayama Labes., Co Ltd.; male; 4-week-old) and soaked into Hank's balanced salt solution (calcium- and magnesium-free; LifeTech Co., Ltd.; hereinafter, referred to as "HBSS"). One costicartilage and one costa were excised together, the adipose tissue and the muscle tissue were removed and then, the proliferating chondrocyte layer of costicartilage was excised. The collected proliferating chondrocyte layer was cut into sections with a surgical knife (FEATHER Safety Razor Co., Ltd.) and the all proliferating chondrocyte layer sections from 4 rabbits were combined in a centrifuge tube. To the centrifuge tube was added 40 ml of HBSS (pH 7.2) supplied with 0.1% tetrasodium ethylenediamine tetraacetate to obtain suspension of the proliferating chondrocyte layer sections, which was shaken at 37° C. for 20 minutes and centrifuged (1500 rpm, 10 minutes). The supernatant was aspirated off, and 40 ml of HBSS (pH 7.2) supplied with 0.2% trypsin was added to the tube to suspend the precipitates and shaken at 37° C. for 1 hour. The tube was centrifuged (1500 rpm, 10 minutes), and the supernatant was aspirated off. The precipitates were washed twice with HBSS, suspended in 100 ml of HBSS supplied with 0.1% collagenase (Wako Pure Chemical Industries, Ltd., 034-10533) and shaken at 37° C. for 3 hours. The content of the tube was passed through the Cell Strainer (pore size 40 μm) and the filtrate was divided into four centrifuge tubes. To each of all four tubes was added 40 ml of medium (α-MEM, LifeTech Co., Ltd.), and the tubes were centrifuged (1500 rpm, 10 minutes). The supernatant was aspirated off, and the resultant precipitates were collected in one tube with Pipetman. After addition of 40 ml of the same medium, the tube was re-centrifuged (1500 rpm, 10 minutes). Washing procedure comprising addition of medium followed by centrifugation was repeated additional three times. The precipitates were suspended in the same medium to give an about 5 ml suspension, and the cell number was counted.

(Cultivation of Costicartilage Cells)

The suspension of costicartilage cell described above was added to 24-well plate at 50,000 cells per well (day 1). Next day, medium was replaced with the same medium. After the medium replacement at day 5, the medium in the well for test sample was replaced with a medium (including 0.1% dimethylsulfoxide as a vehicle) containing a test compound indicated in Table 10 below. At the same time, the medium in the well for control was replaced with the same medium as the above except that it does not contain a test compound (vehicle only). At that time, ascorbate-phosphate ester was added to the medium at 2 mM of final concentration. In the case of Alcian blue staining, medium was changed at 5, 7, 9, 12 and 14 days, and the Alcian blue staining was carried out at day 16 from the initiation of cultivation.

(Cartilage Matrix Production)

After removing the medium, cells in each well were fixed by addition of 1 ml of neutral buffer containing 4% paraformaldehyde and incubation for 30 minutes at room temperature. Cells were then washed twice with 1 ml of phosphate buffer (pH 7.2), and to each well was added 1 ml of pre-filtered 0.1 M HCl containing 0.1% Alcian blue BGX (Sigma; A3157), which stains cartilage matrix proteoglycan selectively. Alcian blue was dissolved by adding 0.5 ml of aqueous 6 M guanidine hydrochloride solution to each well. Absorbance at 620 nm was measured, and cartilage matrix amount (proteoglycan production amount) in each well was estimated, and proteoglycan production rate (%) of each test compound for vehicle (100%) was calculated. The results are shown in Table 10.

TABLE 10

| Test Compound | Concentration (M) | Proteoglycan Production (%) |
|---|---|---|
| Vehicle | — | 100 |
| Compound (1) | $1 \times 10^{-4}$ | 524 |
| Compound (2) | $1 \times 10^{-6}$ | 204 |
| Compound (2) | $1 \times 10^{-5}$ | 906 |
| Compound (9) | $1 \times 10^{-6}$ | 132 |
| Compound (9) | $1 \times 10^{-5}$ | 149 |
| Compound (11) | $1 \times 10^{-6}$ | 161 |
| Compound (11) | $1 \times 10^{-5}$ | 149 |
| Compound (21) | $1 \times 10^{-6}$ | 156 |
| Compound (21) | $1 \times 10^{-5}$ | 339 |
| Compound (27) | $1 \times 10^{-6}$ | 151 |
| Compound (27) | $1 \times 10^{-5}$ | 157 |
| Compound (44) | $1 \times 10^{-5}$ | 185 |
| Compound (44) | $1 \times 10^{-4}$ | 263 |

Experimental Example 4

In Vitro Test

The cartilage matrix (proteoglycan) production was determined using other compounds (compounds (52)-(55) and Compound (2) for comparison) in exactly the same manner as Experimental Example 3 above. The results are shown in Table 11.

TABLE 11

| Test Compound | Concentration (M) | Proteoglycan Production (%) |
|---|---|---|
| vehicle | — | 100 |
| Compound (2) | $1 \times 10^{-7}$ M | 128 |
| Compound (2) | $1 \times 10^{-6}$ M | 183 |

TABLE 11-continued

| Test Compound | Concentration (M) | Proteoglycan Production (%) |
|---|---|---|
| Compound (2) | $1 \times 10^{-5}$ M | 686 |
| Compound (52) | $1 \times 10^{-7}$ M | 213 |
| Compound (52) | $1 \times 10^{-6}$ M | 774 |
| Compound (52) | $1 \times 10^{-5}$ M | 820 |
| Compound (53) | $1 \times 10^{-6}$ M | 729 |
| Compound (54) | $1 \times 10^{-6}$ M | 171 |
| Compound (54) | $1 \times 10^{-5}$ M | 396 |
| Compound (55) | $1 \times 10^{-6}$ M | 171 |
| Compound (55) | $1 \times 10^{-5}$ M | 188 |

As shown in Tables 10 and 11, all the compounds having PDE4 inhibitory activity showed cartilage matrix (proteoglycan) production promoting effect. Above all, Compounds (1), (2), (52) and (53) showed remarkable matrix production promoting effect.

Experimental Example 5

Calcification of Chondrocyte

Cells were treated according to the method described in "Isolation of Costicartilage Cell" and "Cultivation of Costicartilage Cell" described in Experimental Example 3, except that Compound (1) ($10^{-4}$ M) was used as a test compound. The medium in each well was removed and cells were fixed by addition of 1 ml of neutral buffer containing 4% formaldehyde and 30-minute-incubation at room temperature. Wells were washed twice with 1 ml of phosphate buffer (pH 7.2). After adding 5% aqueous silver nitrate solution which selectively stains calcified portion, the wells were incubated at room temperature until development. Each well was washed with distilled water and the reaction was quenched by addition of 5% aqueous sodium thiosulfate solution, wells were washed with distilled water again and then photographed. Cells were fixed with 1 ml of 100% ethanol for 1 hour, stained with 0.1% Alizarin Red solution (from Sigma) in ethanol for 1 hour, washed twice with 100% ethanol and photographed.

The results are shown in FIG. 1. As shown in FIG. 1, when cells were cultured in a medium containing a PDE4 inhibitor, Compound (1), calcium deposition was clearly observed by 4 week cultivation, which demonstrated that Compound (1) has calcification enhancement effects.

Experimental Example 6

Regeneration of Radius Defect in Rabbit (Acclimation)
Japanese White rabbits (male; 11-week-old; 4 rabbits/group) were housed for seven days at room temperature (23±2° C.) and 55±15% humidity. During the housing period, the rabbits were free to access commercially available food (from Oriental Bio Service; LRC4).

(Fracture Healing)
Under pentobarbital sodium anesthesia, radium was separated from muscle tissue of right forearm of a rabbit; periosteum was pealed off, and removed 10 mm of diaphysis by cutting with a bone cutter. To a gelatin capsule (CAPSUGEL, size 5) were filled microspheres prepared in Example 7-(1), which contains 8 μg or 40 μg of Compound (2), and the total amount of microspheres contained in the capsule was adjusted to 15 mg by filling microspheres prepared in Control Example 2. One each capsule was placed at the bone defect portion, the periosteum was repositioned to include the capsules and sutured. In control group, gelatin capsules filled with microspheres prepared in Control Example 2 in the same manner were used. Muscle and skin were each sutured and sterilized. At six weeks after sutura, under pentobarbital anesthesia, rabbits were sacrificed by bleeding and the radiuses were excised.

(Experimental Results)
As to the excised radium of right forearm, the shoulder-side on the fracture line was defined as the proximal end and the point 5 mm apart from the proximal end toward wrist defined as the distal end. The total (cross sectional) bone area (mm²) and stress-strain index (SSI: mm³) at the distal end were determined using pQCT (Norland-Stratec; XCT-960A) (Clinical Calcium Vol. 10, 35-41, 2000).

Figure 2:
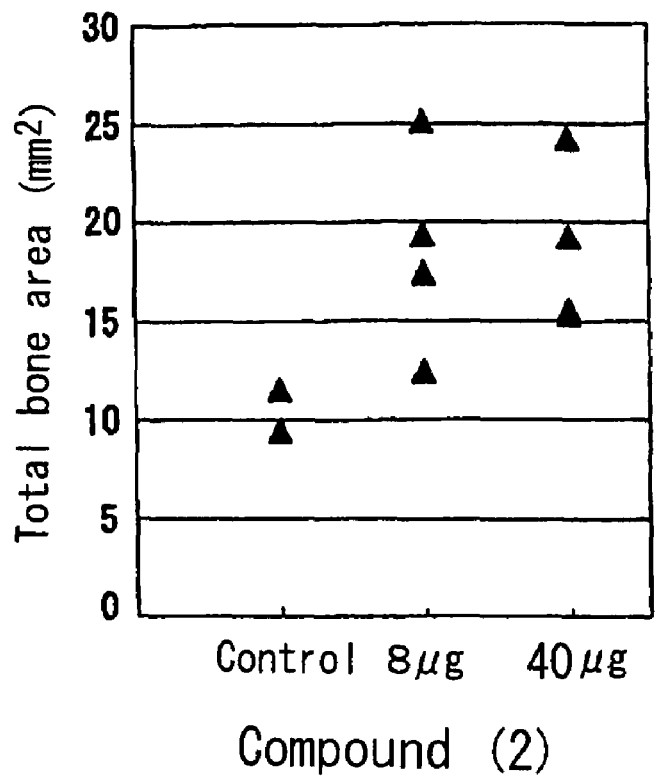
FIG. 2 is a graph showing the reproduction of a defective radius in a rabbit treated with PDE4 inhibitor (Compound (2)) microsphere. The relation between the total bone area (cross sectional) ($mm^2$) or stress-strain index (SSI: $mm^3$), and the dosage of Compound (2) are shown in the upper and the lower graphs, respectively.
Figure 2:
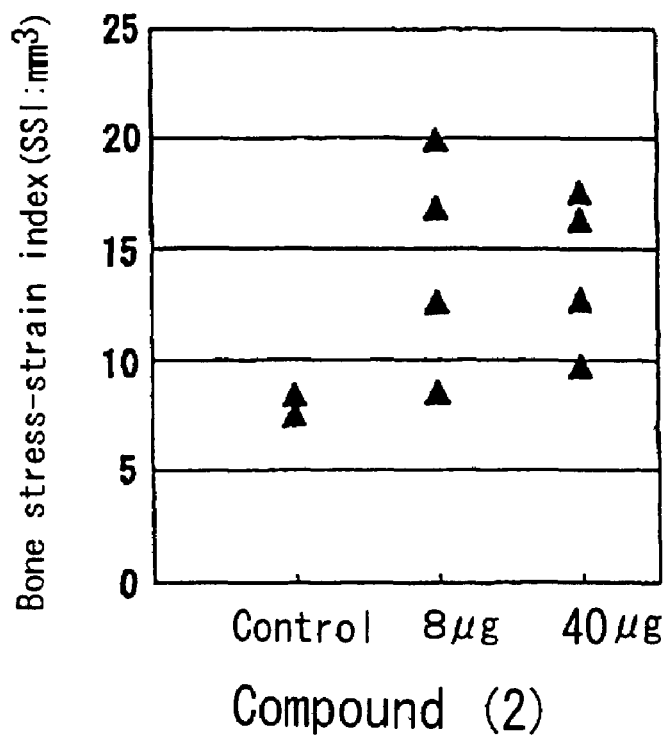

The results are shown in FIG. 2. As shown in FIG. 2, in the group treated with microsphere preparation containing a PDE4 inhibitor of the present invention, both the total cross sectional bone area and stress-strain index improved compared with control group. These results show the effectiveness of PDE4 inhibitor.

Experimental Example 7

Acceleration of Fracture Healing in Diabetic Rat (Acclimation)
CD (SD) IGS rats (Charles River Japan, Inc.; male; 7-week-old) were housed for seven days at room temperature (23±2° C.) and 55±15% humidity. During the housing period, the rats were free to access commercially available food (from Oriental Bio Service; CRF-1).

(Induction of Diabetes)
Streptozotocin (Sigma), which induce diabetes, was dissolved in citrate-buffered saline (pH 4.5) to obtain 0.05 M streptozocin solution and injected intravenously to each rat at 60 mg/kg. One week later, blood was collected from tail end and blood-glucose level was determined with a blood-glucose monitor (Molecular Devices; M-SPmax250). Based on the measurements, rats were divided into groups so that a significant difference in glucose level may not occur among groups. The average blood-glucose level was from 426.12 to 428.23 mg/dl.

(Fracture Healing)
Under ether anesthesia, the left-lower legs of rats were shaved and sterilized with 70% aqueous ethanol, fibulas were exposed with scissors and cut with nail scissors (Natsume Seisakusyo; B17). The cut sections of the fibula were re-matched with tweezers. For the test groups (12 rats/group), the drug-containing microspheres prepared in Example 7-(1), which contains 0.03 or 0.1 mg of Compound (2), were placed around the cutting site using spatula followed by suturing with silk thread. For the control group (12 rats/group), the same amount of drug-free microspheres prepared in Control Example 2 were placed around the cutting site using spatula followed by suturing with silk thread. Following the suturing, every animal was sterilized with 70% aqueous ethanol. After six weeks from the sutura, under ether anesthesia, rats were sacrificed by laparotomy with bleeding, and the fibulas were excised.

(Experimental Results)

Measurements of Fibula Bone Mineral Content

Eight fibulas were randomly selected from those excised at 6 weeks after sutura and subjected to DXA bone densitometer (from Aloka; DCS-600) to determine bone mineral density and bone mineral content at fracture region, (scanning width: 1 mm). The results are shown in Table 12.

TABLE 12

| Drug | Drug Content | Bone mineral content (mg) |
| --- | --- | --- |
| Control | 0 | 10.25 ± 1.27 |
| Compound (2) | 0.03 mg | 13.69 ± 0.96 |
| Compound (2) | 0.1 mg | 14.60 ± 0.69 |

As shown in Table 12, it is found that PDE4 inhibitor has bone mineral content increasing effects in a dose-dependent manner even in the case of bone fracture of diabetic subjects, of which healing is known to be delayed, as demonstrated in the diabetic model animals (Measurements of Fibula Strength)

The fibula used in the determination of mineral content was subjected to a three-point bending test with bone strength tester (from Muromachi Kikai Co., Ltd.; TK-252C) to determine bone strength. Briefly, the fibula was supported by two supports apart from each other by 8 mm and the cut section was positioned at the middle of these supports, i.e., 4 mm apart from the respective two supports. Loading (3 mm/minute) from upper direction was kept on the middle point (fracture section) of fibula until fibula begins to fracture. The maximum pressure necessary to break the bone was defined as the breaking force. The total energy spent to break the bone was defined as the breaking energy. The results are shown in Table 13.

TABLE 13

| Drug | Drug Content | Breaking Force (N) |
| --- | --- | --- |
| Control | 0 | 6.25 ± 0.70 |
| Compound (2) | 0.03 mg | 8.13 ± 1.20 |
| Compound (2) | 0.1 mg | 11.75 ± 2.14 |

| Drug | Drug Content | Breaking Energy (mJ) |
| --- | --- | --- |
| Control | 0 | 0.69 ± 0.08 |
| Compound (2) | 0.03 mg | 1.53 ± 0.39 |
| Compound (2) | 0.1 mg | 2.91 ± 0.82 |

As shown in Table 13, it is found that PDE4 inhibitor increased the breaking force and the breaking energy even in the case of bone fracture of diabetic subjects, of which healing is known to be delayed, as demonstrated in the diabetic model animals (X-Ray Photography)

Four fibulas excised at 6 weeks after sutura was photographed with micro focus magnification radiography system (Fuji Photo Film Co. Ltd.; µFX-1000; tube voltage: 25 kV; tube current: 804A; 20 seconds).

In the control group, the void of bone defect was not filled. In contrast, the void of bone defect was filled and bulging bone was observed in every sample from the test groups.

Experimental Example 8

Increase of cAMP Content at Fracture Region in Normal Rats (Acclimation)

CD (SD) IGS rats (Charles River Japan, Inc.; male; 7-week-old) were housed for seven days at room temperature (23±2° C.) and 55±15% humidity. During the housing period, the rats were free to access commercially available food (from Oriental Bio Service; CRF-1).

(Fracture Healing)

Under ether anesthesia, the left-lower legs of rats were shaved and sterilized with 70% aqueous ethanol, fibulas were exposed with scissors and cut with nail scissors (Natsume Seisakusyo; B17). The cut sections of the fibula were re-matched with tweezers. For the treated group (test compound-administered group) (6 rats/group), the drug-containing microspheres prepared in Example 7-(1), which contains 0.1 mg of Compound(2), were placed around the cutting site using spatula followed by suturing with silk thread. For the non-treated group (6 rats/group), the same amount of drug-free microspheres prepared in Control Example 2 were placed around the cutting site using spatula followed by suturing with silk thread. Regarding control group (6 rats/group), the cut sections were re-matched with tweezers and sutured with silk thread without any treatment. Following the suturing, all animals were sterilized with 70% aqueous ethanol. At 0, 3, 7, 13, 28 or 42 days after suturing, six rats from each group were sacrificed by laparotomy with bleeding under ether anesthesia and the fibula was excised.

(Measurement of cAMP Content)

The fracture segment of the excised fibula was cut into 1 cm sections and frozen with liquid nitrogen. The resultant sections were milled at −80° C., suspended in 300 µl of 6% trichloroacetic acid, and sonicated. The suspension was centrifuged at 12000 rpm for 15 minutes. The supernatant was extracted with ether to remove trichloroacetic acid and incubated at 75° C. for 5 minutes to remove ether from the supernatant. The cAMP in the resultant supernatant was measured using cAMP EIA system (Amersham Pharmacia Biotech).

(Experimental Results)

Figure 3:
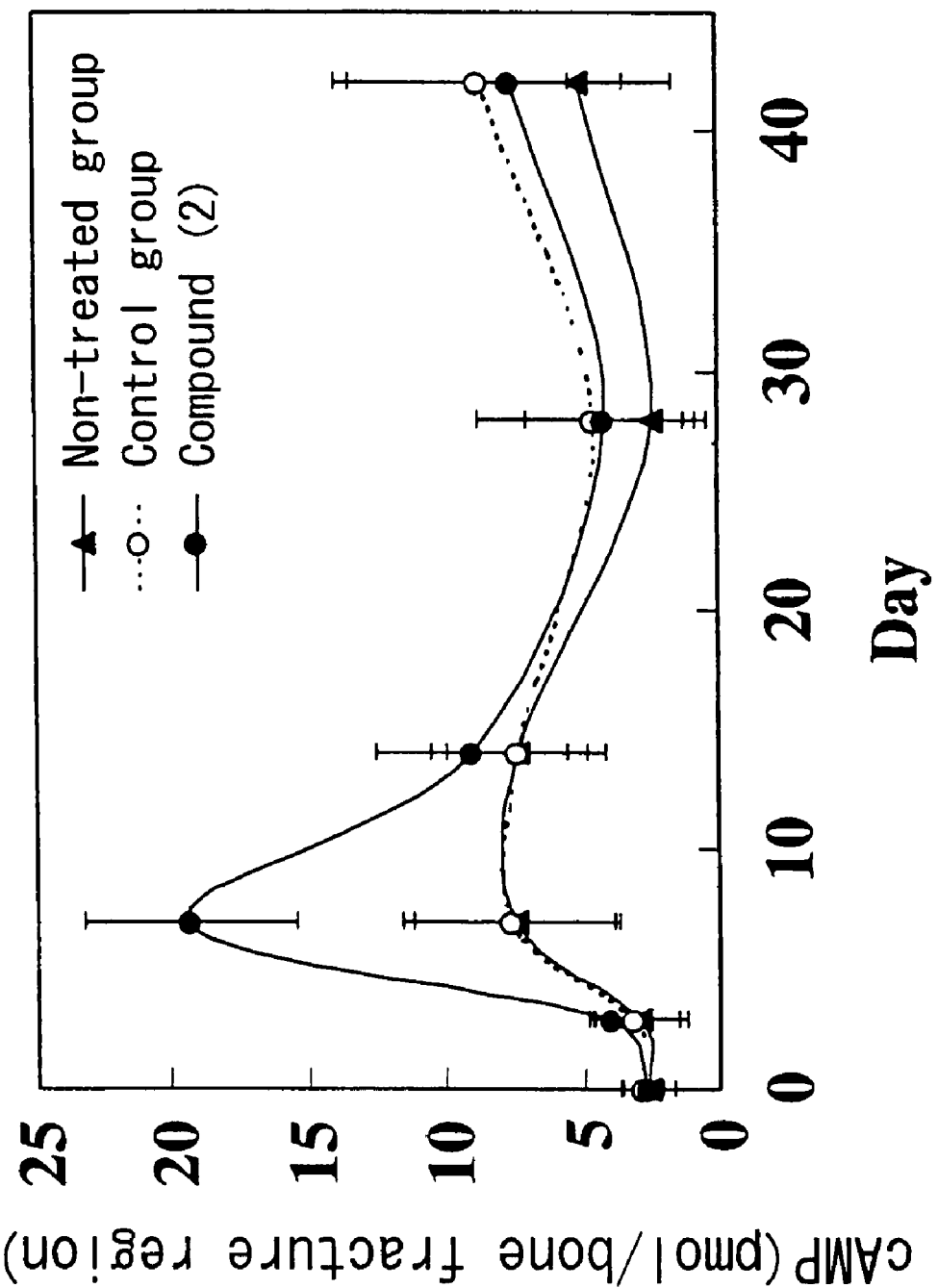
FIG. 3 is a graph showing a time-course of cAMP content in rat fibula fracture region that was treated with a PDE4 inhibitor (Compound (2)) microsphere.

The results of cAMP measurement are shown in FIG. 3. As shown in FIG. 3, in the PDE4-non-treated group (▲) and control group (○), the quantity of cAMP (cAMP content) gently increased and, after the peak on day 7, decreased gradually. On the other hand, in the treated group (●), cAMP content increased remarkably to reach its peak on day 7 and promptly returned to the same level as the control group. These results suggest that the decomposition of intracellular cAMP is prevented by a PDE4 inhibitor, which led to the increase of cAMP content at the fracture region.

Experimental Example 9

Increase of cAMP Content at Fracture Region in Diabetic Rat (Acclimation)

CD (SD) IGS rats (Charles River Japan, Inc.; male; 8-week-old) were housed for seven days at room temperature (23±2° C.) and 55±15% humidity. During the housing period, the rats were free to access commercially available food (from Oriental Bio Service; CRF-1).

(Induction of Diabetes)

Streptozotocin ("STZ", Sigma), which induce diabetes, was dissolved in citrate-buffered saline (pH 4.5) to obtain 0.05 M streptozocin solution and injected intravenously to each rat at 60 mg/kg. One week later, blood was collected from tail end and blood-glucose level was determined with a blood-glucose monitor (Molecular Devices; M-SPmax250). Based on the measurements, rats were divided into groups so that a significant difference in glucose level may not occur among groups. The average blood-glucose level was from 404.5 to 410.00 mg/dl.

(Fracture Healing)

Under ether anesthesia, the left-lower legs of diabetic rats (5 groups, 5 rats/group) and normal (non-treated) rats (5 groups, 5 rats/group) were shaved and sterilized with 70% aqueous ethanol, fibulas were exposed with scissors and cut with nail scissors (Natsume Seisakusyo; B17). The cut sections of the fibula were matched with tweezers followed by suturing with silk thread. Following the suturing, all animals were sterilized with 70% aqueous ethanol. At 0, 3, 7, 14 or 28 days after suturing, five rats from each group were sacrificed by laparotomy with bleeding under ether anesthesia and the fibula was excised.

(Measurement of cAMP Content)

The fracture segment of the excised fibula was cut into 1 cm sections and frozen with liquid nitrogen. The resultant sections were milled at −80° C., suspended in 300 µl of 6% trichloroacetic acid, and sonicated. The suspension was centrifuged at 12000 rpm for 15 minutes. The supernatant was extracted with ether to remove trichloroacetic acid and incubated at 75° C. for 5 minutes to remove ether from the supernatant. The cAMP in the resultant supernatant was measured using cAMP EIA system (Amersham Pharmacia Biotech).

(Experimental Results)

Figure 4:
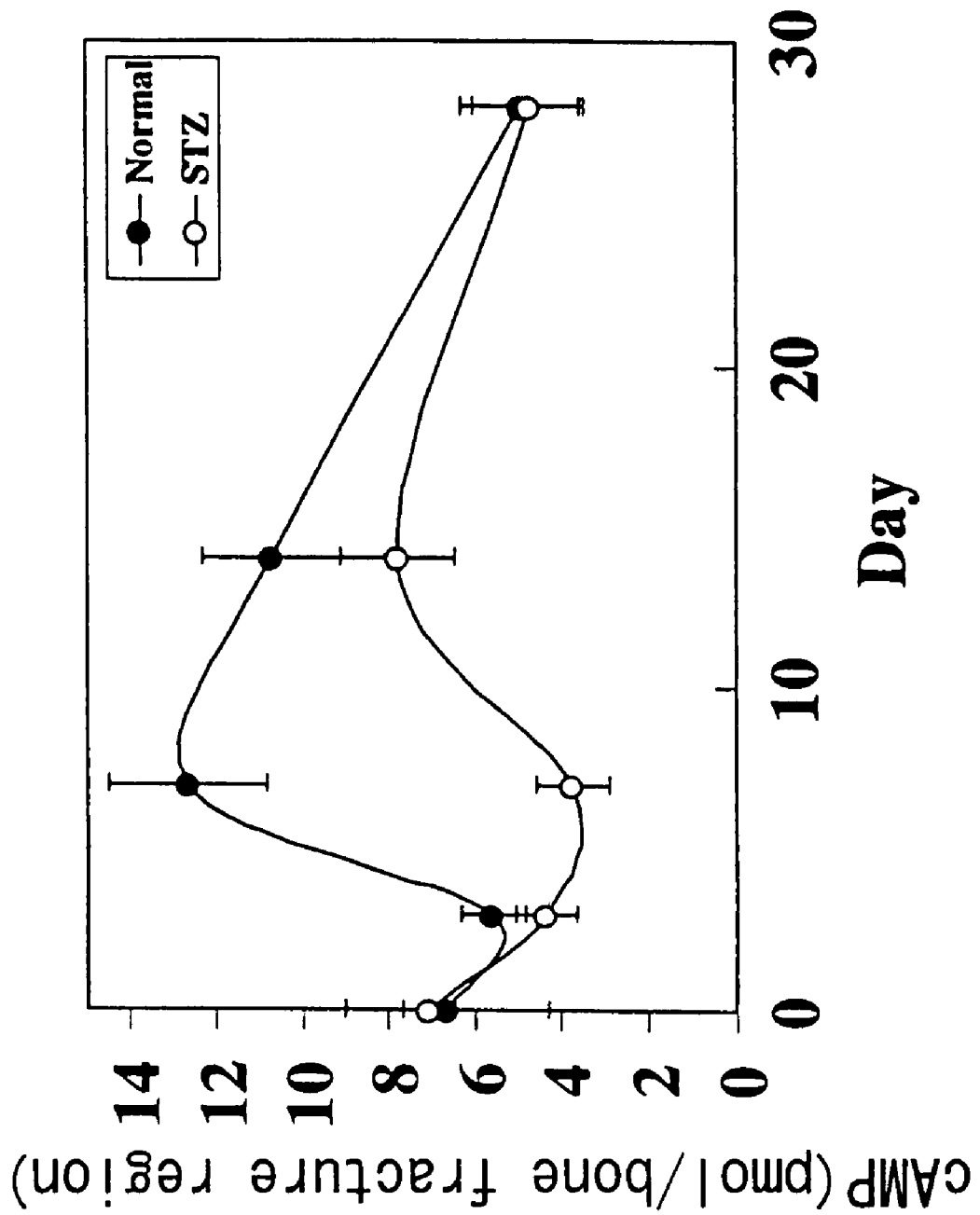
FIG. 4 is a graph showing a time-course of cAMP content in fibula fracture region of normal and STZ-induced diabetic rats.

The results of cAMP measurement (showing the cAMP content at the fracture region) in STZ-treated group (diabetic rats) (○) and non-treated group (normal rats) (●) after treatment with PDE4 inhibitor are shown in FIG. 4.

Example 1

(1) To 0.1 g of Compound (1) and 1.9 g of lactic acid-glycolic acid copolymer (lactic acid:glycolic acid 50:50; average molecular weight 20,000; PLGA5020: Wako Pure Chemical Industries, Ltd.) was added 4.0 g of methylene chloride, and the mixture was shaken for 30 minutes thoroughly to form an oil phase (O).

(2) The oil phase was added to 8 ml of 0.5% aqueous solution of polyvinyl alcohol (POVAL PVA-220C: Kuraray Co., Ltd.) and emulsified at 25° C. for 5 minutes with homogenizer (Polytron, Kinematica A.G.) to form (O/W) emulsion, wherein the oil phase is dispersed in the water phase.

(3) The emulsion was added to 1000 ml of distilled water, stirred at 400 rpm with Three-one motor (Shinto Scientific Co., Ltd.) and subjected to in-water drying method at 25° C. for 3 hours to remove methylene chloride.

(4) The resultant microsphere suspension was filtered through 150 µm filter to remove aggregates and filtered under reduced pressure through 20 µm filter to remove the water phase. The resultant microsphere was combined with a little amount of distilled water and lyophilized to give 1.6 g of microsphere.

Ten mg of the resultant microsphere was dissolved in 3 ml of acetonitrile. The solution was combined with 7 ml of 0.5 M aqueous sodium chloride solution, stirred with a mixer (Touch mixer MT-51: YAMATO Scientific Co., Ltd.) and then centrifuged at 2000 rpm for 5 minutes to separate supernatant. A portion of supernatant was loaded on FL-HPLC (column; Hypersil 5-ODS, diameter: 4 mm, length: 300 mm, GL Sciences, Inc., excitation wavelength: 315 nm, fluorescence wavelength: 465 nm) and the drug concentration in the supernatant was determined by comparing with a standard curve prepared separately with a drug solution. On the basis of the resultant concentration and the volume of supernatant, the drug content in microsphere was estimated as 4.21%.

An adequate amount of resulting microsphere was dispersed in a dilute solution of polyoxyethylene sorbitan fatty-acid ester (Tween 80: Nikko Chemicals Co., Ltd.) The particle distribution was measured with a particle size analyzer SALD-1100 (Shimadzu Corporation), and the average particle size was calculated. The average particle size was 57 µm.

(5) The microsphere obtained in (4) above was added to physiological saline (dispersion medium) containing 0.5% carboxymethyl cellulose sodium (Nichirin Chemical Industries) and 0.1% polyoxyethylene sorbitan fatty acid ester (Tween 80: Nikko Chemicals Co., Ltd.) at final drug concentration of 2.5 mg/ml, and the mixture was stirred with a mixer (Touch mixer MT-51: YAMATO Scientific Co., Ltd.) thoroughly to yield microsphere dispersion.

Example 2

(1) Microsphere (1.6 g) was prepared in a manner similar to that described in Example 1-(1) to (4) except that a mixture of 0.57 g of lactic acid-glycolic acid copolymer (lactic acid: glycolic acid=0.50:50; average molecular weight 20,000; PLGA5020: Wako Pure Chemical Industries, Ltd.) and 1.33 g of lactic acid polymer (average molecular weight 20,000; PLA0020: Wako Pure Chemical Industries, Ltd.) was used.

The drug content and the average particle size of microsphere were measured in a manner similar to that described in Example 1-(4) and proved to be 3.70% and 47.7 µm, respectively.

(2) The microsphere obtained in (1) above was treated in a manner similar to that described in Example 1-(5) to give microsphere dispersion (drug rate: 2.5 mg/ml).

Example 3

(1) Microsphere (1.5 g) was prepared in a manner similar to that described in Example 1-(1) to (4) except that lactic acid polymer (average molecular weight 20,000; PLA0020: Wako Pure Chemical Industries, Ltd.) was used.

The drug content and the average particle size of microsphere were measured in a manner similar to that described in Example 1-(4) and proved to be 3.73% and 52.2 µm, respectively.

(2) The microsphere obtained in (1) above was treated in a manner similar to that described in Example 1-(5) to give microsphere dispersion (drug rate: 2.5 mg/ml).

Example 4

(1) To 0.2 g of Compound (1) and 0.3 g of lactic acid polymer (average molecular weight 20,000; PLA0020: Wako Pure Chemical Industries, Ltd.) was added 1.0 g of methylene chloride, and the mixture was shaken with a mixer (Touch mixer MT-51: YAMATO Scientific Co., Ltd.) thoroughly to form an oil phase (O).

(2) The oil phase was added to 4 ml of 0.25% aqueous solution of methyl cellulose (METOLOSE: Shin-Etsu Chemical Co., Ltd.) and emulsified at 25° C. for 5 minutes with homogenizer (Polytron, Kinematica A.G.) to form (O/W) emulsion, wherein the oil phase is dispersed in the water phase.

(3) The emulsion was added to 400 ml of distilled water, stirred at 400 rpm with Three-one motor (Shinto Scientific Co., Ltd.) and subjected to in-water drying method at 25° C. for 3 hours to remove methylene chloride.

(4) The resultant microsphere suspension was filtered through 150 μm filter to remove aggregates and filtered under reduced pressure through 20 μm filter to remove water phase. The resultant microsphere was combined with a little amount of distilled water and lyophilized to give microsphere. The drug content and the average particle size of microsphere were measured in a manner similar to that described in Example 1-(4) and proved to be 39.6% and 33.4 μm, respectively.

Example 5

(1) To 0.05 g of Compound (1) and 0.45 g of lactic acid-glycolic acid copolymer (lactic acid:glycolic acid=50:50; average molecular weight 20,000; R202H: Boehringer Ingelheim Co., Ltd.) was added 1.0 g of methylene chloride, and the mixture was shaken with a mixer (Touch mixer MT-51: YAMATO Scientific Co., Ltd.) thoroughly to form an oil phase (O).

(2) The oil phase was added to 40 ml of 0.5% aqueous solution of polyvinyl alcohol (GOHSENOL EG-40: The Nippon Synthetic Chemical Industry Co., Ltd.) and emulsified at 25° C. for 4 minutes with homogenizer (Polytron, Kinematica A.G.) to form (O/W) emulsion, wherein the oil phase is dispersed in the water phase.

(3) Emulsion was poured into a cylindrical airtight container (inside diameter: 110 mm; volume 1,000 ml) containing 400 ml of purified water, and methylene chloride was removed from the container by stirring at 25° C. and 400 rpm using 4-bladed propeller (diameter: 50 mm, propeller R type: HEIDON) equipped with Three-one motor (BL-600; HEIDON) while supplying nitrogen gas into hollow fibers of cylinder-type hollow fiber membrane module made of silicone rubber (NAGAYANAGI Co., Ltd.) inserted in the container (gas flow rate is 2 L/minute). This procedure was conducted for 1 hour.

The cylindrical hollow fiber membrane module made of silicone rubber used in this procedure is cylinder type NAGASEP M60-1800 of the following specification.

| | |
|---|---|
| Cylinder diameter | 100 mm |
| Cylinder length | 120 mm × 120 mm |
| Membrane thickness of hollow fiber membrane | 60 μm |
| Inside diameter of hollow fiber membrane | 200 μm |
| Outside diameter of hollow fiber membrane | 320 μm |
| Number of hollow fiber | 1800 |
| Effective membrane area of hollow fiber membrane | 0.15 m$^2$ |

(4) The resulting microsphere suspension was filtered through 150 μm filter to remove aggregates and filtered under reduced pressure through 20 μm filter to remove water phase. The resultant microsphere was combined with a little amount of distilled water and lyophilized to give 0.26 g of microsphere. The drug content and the average particle size of microsphere were measured in a manner similar to that described in Example 1-(4) and proved to be 3.07% and 71.7 μm, respectively.

Example 6

(1) To 0.05 g of Compound (2) and 0.45 g of lactic acid-glycolic acid copolymer (lactic acid:glycolic acid=50:50; average molecular weight 20,000; RG502H: Boehringer Ingelheim Co., Ltd.), 2.5 g of methylene chloride was added and shaken with a mixer (Touch mixer MT-51: YAMATO Scientific Co., Ltd.) thoroughly to form an oil phase (O).

(2) The oil phase was added to 3 ml of 0.5% aqueous solution of polyvinyl alcohol (POVAL PVA-220C: Kuraray Co., Ltd.) and emulsified at 22° C. for 5 minutes with homogenizer (Polytron: Kinematica A.G.) to form (O/W) emulsion, wherein the oil phase was dispersed in the water phase.

(3) The above procedures (1) and (2) were repeated five times. The resultant emulsions (from 5 trials) were combined, added to 1000 ml of distilled water, and stirred at 400 rpm with Three-one motor (Shinto Scientific Co., Ltd.) to remove methylene chloride by conducting in-water-drying at 25° C. for 1.5 hours, at 40° C. for 1 hour and at 25° C. for 0.5 hours.

(4) The resultant microsphere suspension was filtered through 150 μm filter to remove aggregates and filtered under reduced pressure through 20 μm filter to remove water phase. The resultant microsphere was combined with a little amount of distilled water and lyophilized to give 2.3 g of microsphere.

Ten mg of the resultant microsphere was dissolved in 3 ml of acetonitrile. The solution was combined with 6 ml of 0.5 M aqueous sodium chloride solution, stirred with a mixer (Touch mixer MT-51: YAMATO Scientific Co., Ltd.) and then centrifuged at 2000 rpm for 5 minutes to separate supernatant. A portion of supernatant was loaded on UV-HPLC (column; Hypersil 5-ODS, diameter: 4 mm, length: 300 mm, GL Sciences, Inc., detection wavelength: 240 nm) and the drug concentration in the supernatant was determined by comparing with a standard curve prepared separately with a drug solution. On the basis of the resultant concentration and the volume of supernatant, the drug content in microsphere was estimated. Further, the average particle size was measured in a manner similar to that described in Example 1-(4). As a result, the drug content was 9.9% and the average particle size was 26.4 μm.

(5) The microsphere obtained in (4) above was treated in a manner similar to that described in Example 1-(5) to give microsphere dispersion (drug rate: 0.1 mg/ml).

Example 7

(1) Microsphere (2.2 g) was prepared in a manner similar to that described in Example 6-(1) to (4) except that lactic acid-glycolic acid copolymer (lactic acid:glycolic acid 75:25; average molecular weight 20,000; PLGA7520: Wako Pure Chemical Industries, Ltd.) was used and that 2.0 g of methylene chloride was added.

The drug content and the average particle size of microsphere were measured in a manner similar to that described in Example 6-(4) and proved to be 10.1% and 27.0 μm, respectively.

(2) The microsphere obtained in (1) above was treated in a manner similar to that described in Example 6-(5) to give microsphere dispersion (drug rate: 0.1 mg/ml).

Control Example 1

Control of Example 2

(1) To 0.6 g of lactic acid-glycolic acid copolymer (lactic acid:glycolic acid=50:50; average molecular weight 20,000; PLGA5020: Wako Pure Chemical Industries, Ltd.) and 1.4 g of lactic acid polymer (average molecular weight 20,000) was added 4.0 g of methylene chloride, and the mixture was shaken for 30 minutes thoroughly to form an oil phase (O). In accordance with the procedures described in Example 1-(1) to (4), 1.7 g of microsphere free of drug was obtained.

(2) Preparation of Placebo Dispersion Solution

The microsphere obtained in (1) above was treated in a manner similar to that described in Example 1-(5) to prepare microsphere dispersion.

Control Example 2

Control of Example 7

To 0.45 g of lactic acid-glycolic acid copolymer (lactic acid:glycolic acid=75:25; average molecular weight 20,000; PLGA7520: Wako Pure Chemical Industries, Ltd.) was added 2.0 g of methylene chloride, and the mixture was shaken with a mixer (Touch mixer MT-51: YAMATO Scientific Co., Ltd.) thoroughly to form an oil phase. In accordance with the procedures described in Example 6-(2) to (4), 2.2 g of microsphere free of drug was obtained.

Test Example 1

To 10 mg of microsphere in a test tube was added 10 ml of phosphate buffered saline (pH 7.4) containing 0.05% Tween 80, and stirred with a rotating cultivator at 25 rpm in an air-temperature-controlled cabinet at 37° C. When a defined period of time passed from the initiation of stirring, test tube was centrifuged (2000 rpm, 5 min) and 9 ml of supernatant was sampled and loaded on FL-HPLC (column; Hypersil 5-ODS, diameter: 4 mm, length: 300 mm, GL Sciences, Inc., excitation wavelength: 315 nm, fluorescence wavelength: 465 nm) and the drug content was determined by comparing with a standard curve prepared separately with a drug solution. On the basis of the result and the sampling volume, the elution amount of drug was estimated.

Further, the estimation of elution amount of drug was repeated regularly by adding 9 ml of phosphate buffered saline (pH 7.4) to the test tube after sampling, and conducting the same procedures under the same conditions, which comprises stirring, sampling, and estimating.

After the final sampling, the remaining eluate was removed from the test tube and the drug content in the residual microsphere was determined according to the method described in Example 1-(4).

Figure 5:
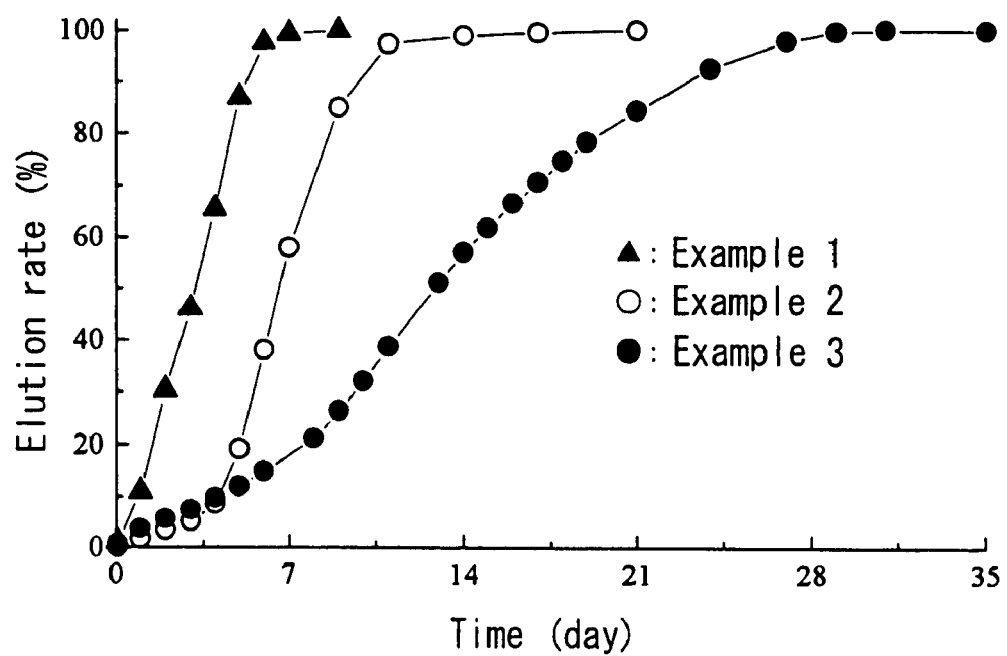
FIG. 5 is a graph showing the in vitro elution characteristics of microspheres obtained in Example 1-(4), 2-(1) and 3-(1).

The above procedures were carried out on the microspheres obtained in Examples 1 to 3. The results are shown in FIG. 5.

The elution rate was calculated based on the assumption that the sum of drug eluted from and remained in the microsphere being 100%.

Test Example 2

Male SD rats (7-weeks-old, 3 rats/group, Japan SLC) were conditioned for a week by housing at room temperature (23±2° C.) under 12 hours light-dark cycle while feeding with food and water ad libitum. Each rat then received rapid-injection of Compound (1) (1 mg/ml) dissolved in physiological saline containing 10% polyethylene glycol 400 ((Wako Pure Chemical Industries, Ltd.) from femoral vein at 0.5 ml/animal (total drug dosage: 0.5 mg/rat).

Figure 6:
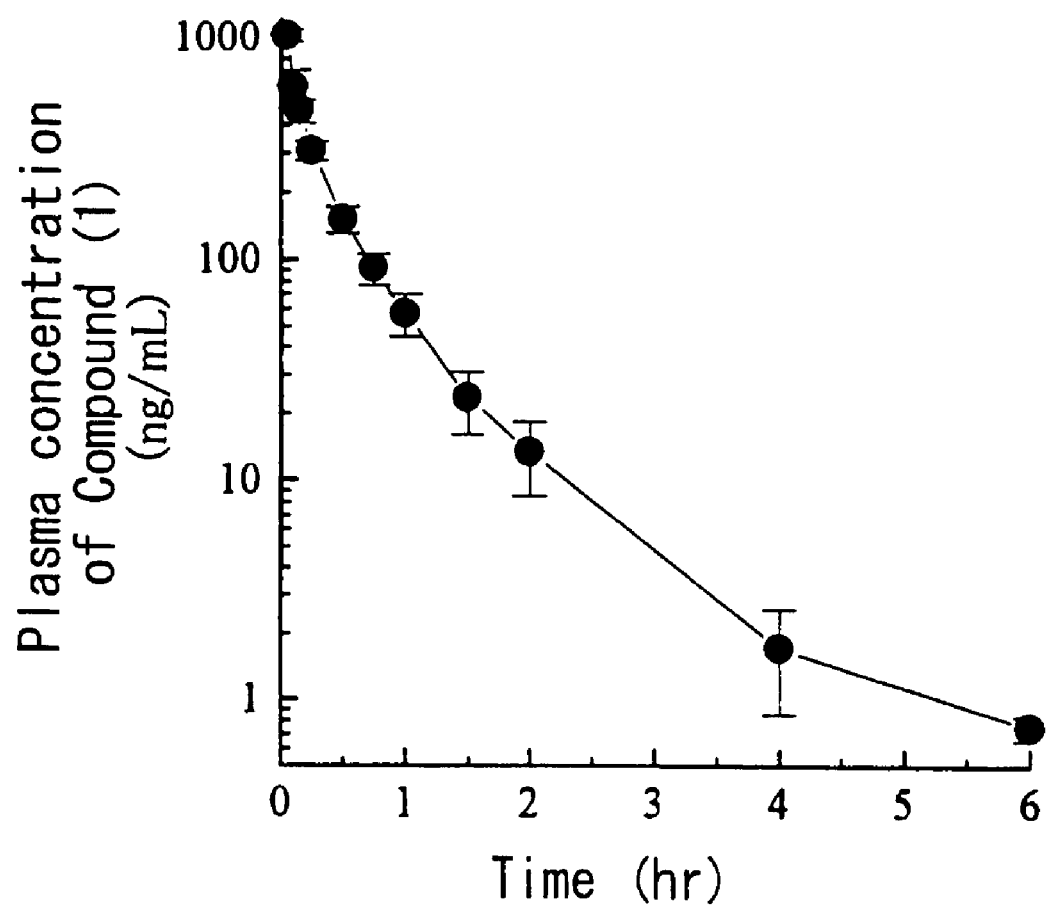
FIG. 6 is a graph showing the time-course of plasma concentration of Compound (1) administered intravenously. Data are shown by mean ±standard deviation (n=3).

After drug administration, under ether anesthesia blood samples were collected at regular time intervals from jugular vein with a syringe containing heparin and centrifuged to obtain plasma samples. To 0.1 ml of plasma were added 0.2 ml of internal standard solution and 1 M dibasic potassium phosphate and then 7.0 ml of chloroform. The mixture was shaken for 10 minutes and centrifuged for 5 minutes to separate 5 ml of organic phase. The resultant organic phase was evaporated to dryness at 40° C. under nitrogen atmosphere, re-dissolved in 0.5 ml of mobile phase and then loaded on FL-HPLC (column; Hypersil 5-ODS, diameter: 4 mm, length: 300 mm, GL Sciences, Inc., excitation wavelength: 315 nm, fluorescence wavelength: 465 nm) to determine the plasma concentration. The results are shown in FIG. 6.

Test Example 3

Figure 7:
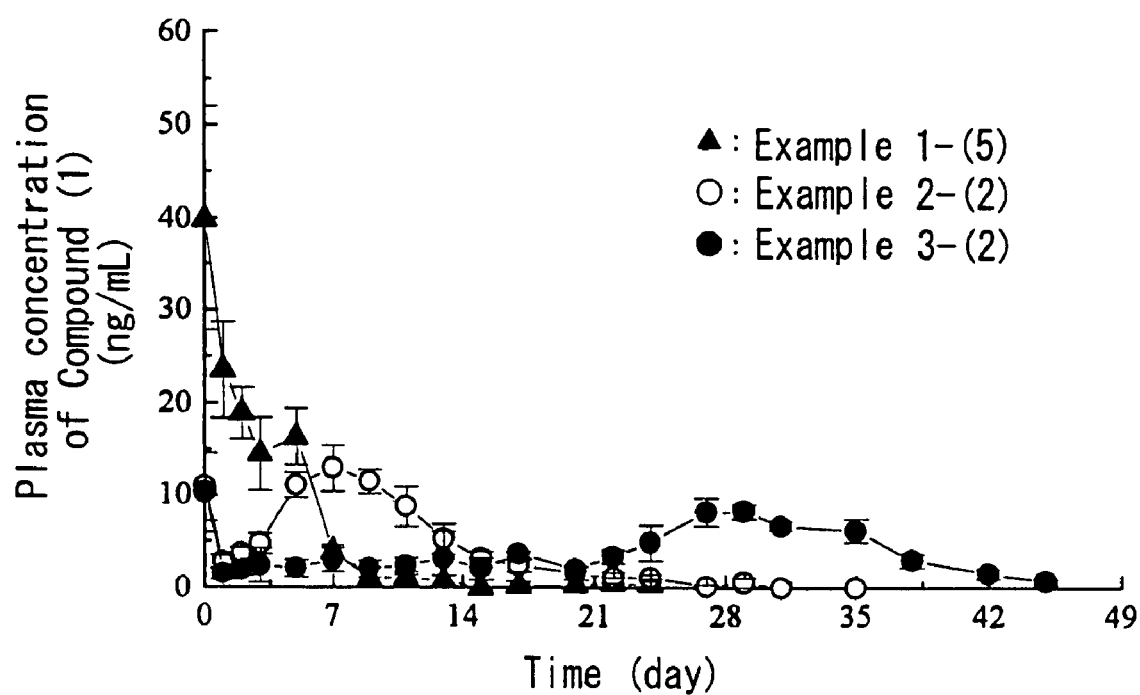
FIG. 7 is a graph showing the time-course of plasma concentration of an active ingredient following the subcutaneous injection of microsphere dispersion obtained in Example 1-(5), 2-(2) or 3-(2). Data are shown by mean ±standard deviation (n=5).

Male SD rats (7-weeks-old, 5 rats/group, Japan SLC) were conditioned for a week by housing at room temperature (23±2° C.) under 12 hours light-dark cycle while feeding with food and water ad libitum. Each rat then received subcutaneously microsphere dispersion obtained in Examples 1-(5), 2-(2) or 3-(2) from back at 2 ml per rat (total drug dosage: 5 mg/rat). After drug administration, under ether anesthesia, blood samples were collected at regular time intervals from jugular vein with a syringe containing heparin and centrifuged to obtain plasma samples. The concentration of the compound in plasma was determined in a manner similar to that described in Test Example 2. As a result of formulating PDE4 inhibitor into microsphere, the maximum plasma concentration of PDE4 inhibitor could be reduced to 1/25 to 1/100, even when compared with that achieved by intravenous injection of saline containing only a tenth amount of PDE4 inhibitor (Test Example 2). The results are shown in FIG. 7.

Test Example 4

Male SD rats (7-weeks-old, 5 rat per group, Japan SLC) were conditioned for a week by housing at room temperature (23±2° C.) under 12 hours light-dark cycle while feeding with food and water ad libitum. Each rat then received subcutaneously microsphere dispersion obtained in Example 2-(2) from back at 2 ml per rat (total drug dosage: 5 mg/rat).

Figure 8:
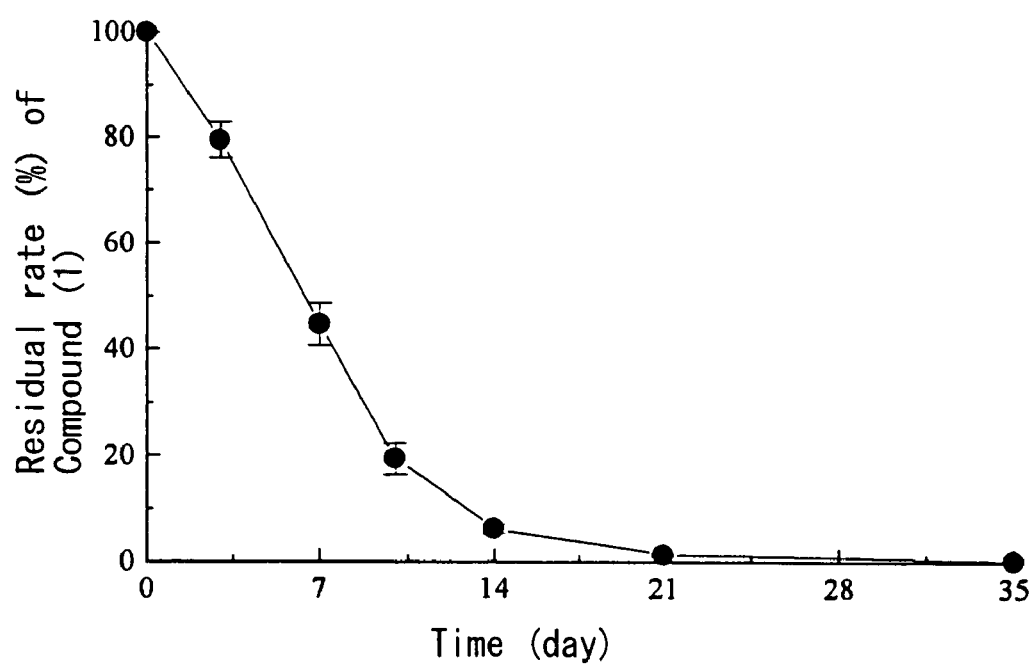
FIG. 8 is a graph showing the time-course of Compound (1) remaining in the preparation following the subcutaneous injection of microsphere dispersion obtained in Example 2-(2). Data are shown by mean ±standard deviation (n=5).

At days 3, 7, 10, 14, 21 and 35 after drug administration, microspheres were collected from the sites of administration. To the collected microspheres, 5 ml of acetonitrile containing internal control substance was added and dissolved with homogenizer (Polytron: Kinematica A.G.). After centrifugation at 3,000 rpm, 5 minutes, 3 ml of supernatant was collected, combined with 7 ml of 0.5 M aqueous sodium chloride solution, stirred with a mixer (Touch mixer MT-51: YAMATO Scientific Co., Ltd.) and then centrifuged at 2,000 rpm for 5 minutes to separate supernatant. A portion of supernatant was filtrated through KC prep-omni 13 (Katayama Chemistry Inc.) and loaded on FL-HPLC (column; Hypersil 5-ODS, diameter: 4 mm, length: 300 mm, GL Sciences, Inc., excitation wavelength: 315 nm, fluorescence wavelength: 465 nm). The drug concentration was determined by comparing with a standard curve prepared separately with a drug solution. On the basis of the resultant concentration and the volume of supernatant, the residual rate of a drug remaining in microsphere was calculated. The results are shown in FIG. 8.

Test Example 5

Male SD rats (7-weeks-old, Japan SLC) were conditioned for a week by housing at room temperature (23±2° C.) under 12 hours light-dark cycle while feeding with food and water ad libitum. Each rat then received subcutaneously Compound (2)-containing microsphere dispersions obtained in Examples 6-(5) and 7-(2) at 1 ml per rat (total drug dosage: 0.1 mg/rat) from back.

Figure 9:
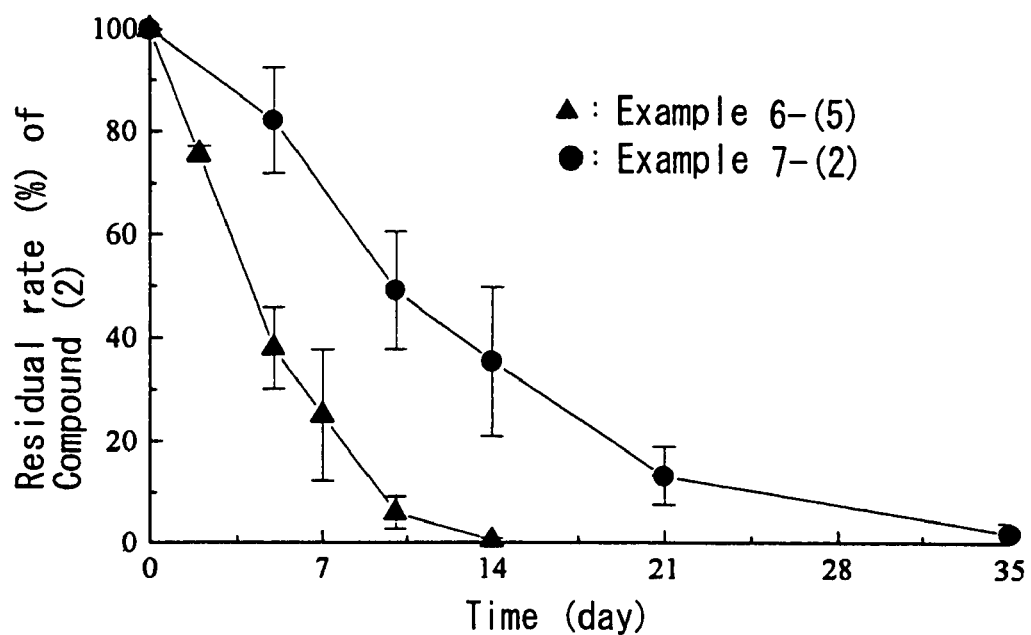
FIG. 9 is a graph showing the time-course of Compound (2) remaining in the preparation following the subcutaneous injection of microsphere dispersion obtained in Example 6-(5) or 7-(2). Data are shown by mean ±standard deviation (n=4).

Microspheres were collected at regular time intervals from the administration site. To the collected microspheres, 10 ml of acetonitrile was added and dissolved with homogenizer (Polytron: Kinematica A.G.). After centrifugation at 3,000 rpm for 5 minutes, 3 ml of supernatant was collected, combined with 6 ml of 0.5 M aqueous sodium chloride, stirred with a mixer (Touch mixer MT-51: YAMATO Scientific Co., Ltd.) and then centrifuged at 2000 rpm for 5 minutes to separate supernatant. A portion of supernatant was filtrated through KC prep-omni 13 (Katayama Chemistry Inc.) and loaded on UV-HPLC (column; Hypersil 5-ODS, diameter: 4 mm, length: 300 mm, GL Sciences, Inc., detection wavelength: 240 nm). The drug concentration was determined by comparing with a standard curve prepared separately with a drug solution. On the basis of the resultant concentration and the volume of supernatant, the residual rate of a drug remaining in microsphere was calculated. The results are shown in FIG. 9.

INDUSTRIAL APPLICABILITY

The bone fracture healing accelerating composition of the present invention comprises a PDE4 inhibitor as an active ingredient, which, when administered locally to the fracture region, can promote the fracture healing by accelerating the endochondral ossification in the reparative phase without producing side effects due to systemic action of PDE4 inhibitor, and can accelerate the healing of bone fracture of elderly people, and diabetic or osteoporosis patients in the early stage, which bone fracture is becoming a major social issue of recent years, whereby exerts an effect of preventing the patients from becoming bedridden and ensures their normal daily life. Still higher effect can be achieved by formulating a composition containing a PDE4 inhibitor and a biocompatible and biodegradable polymer into a depot preparation, especially into an injectable microsphere preparation and administering the same locally to a fracture region thereby allowing efficacy to last.

The invention claimed is:

1. A method for accelerating bone fracture healing in a patient in need thereof, comprising administering to the patient a composition containing a PDE (phosphodiesterase) 4 inhibitor as an active ingredient.

2. The method according to claim 1, wherein the administering comprises administering the composition locally at the fracture region and the composition is a composition configured for gradually releasing the PDE4 inhibitor.

3. The method according to claim 2, wherein the composition comprises a biocompatible and biodegradable polymer.

4. The method according to claim 3, wherein the biocompatible and biodegradable polymer is water-insoluble.

5. The method according to claim 4, wherein the composition comprises is in the form of microspheres comprising the PDE4 inhibitor.

6. The method according to claim 5, wherein the microsphere particle size is 0.1-150 μm.

7. The method according to claim 5 or 6, wherein the composition comprises the PDE4 inhibitor in an amount of 0.0001-80% by weight of the total composition.

8. The method according to claim 4, wherein the water-insoluble biocompatible and biodegradable polymer is a hydroxy fatty acid polyester.

9. The method according to claim 8, wherein the water-insoluble biocompatible and biodegradable polymer is one or more polymers selected from the group consisting of poly lactic acid, lactic acid-glycolic acid copolymer and 2-hydroxybutyric acid-glycolic acid copolymer.

10. The method according to claim 8 or 9, wherein the water-insoluble biocompatible and biodegradable polymer has an average molecular weight of 2000-800000.

11. The method according to claim 5, wherein the composition is an injectable microsphere preparation comprising the microspheres at a concentration of 0.0001-1000 mg/ml in an aqueous solution comprising a dispersant.

12. The method according to claim 11, wherein the injectable microsphere preparation comprises the dispersant at a concentration of 0.01-2% by weight.

13. The method according to claim 11 or 12, wherein the dispersant is one or more selected from the group consisting of polyoxyethylene sorbitan fatty acid ester, polyethylene castor oil, carboxymethyl cellulose sodium, sodium alginate, dextran and sodium hyaluronate.

14. The method according to claim 1, wherein the PDE4 inhibitor is a selective PDE4 inhibitor.

15. The method according to claim 1, wherein $IC_{50}$ of the PDE4 inhibitor is less than 100 nM.

16. The method according to claim 1, wherein the PDE4 inhibitor is a compound having a partial structure having PDE4 inhibitory activity as follows:

(A) naphthalene or an analogous chemical structure thereof; or (B) 3-cyclopentyloxy-4-methoxyphenyl or an analogous chemical structure thereof.

17. The method according to claim 1, wherein the PDE4 inhibitor has a partial structure of a naphthalene or an isoquinoline skeleton or a pharmaceutically acceptable salt thereof.

18. The method according to claim 17, wherein the PDE4 inhibitor is 2,3-bis(hydroxymethyl)-6,7-diethoxy-1-[1-(2-methoxyethyl)-2-oxo-4-pyridyl]naphthalene or 2,3-bis(hydroxymethyl) -6,7-diethoxy-1-[2-(4-(3-pyridyl)-1(2H)-phthaladinon-2-yl)-4-pyridyl]naphthalene or a pharmaceutically acceptable salt thereof.

19. A method for preparing a lyophilized PDE4 inhibitor preparation, comprising suspending microspheres comprising a PDE4 inhibitor as an active ingredient and a biocompatible and biodegradable polymer into an aqueous solution comprising an aggregation inhibitor, and lyophilizing the resultant suspension.

20. The method according to claim 1, where the PDE4 inhibitor is a compound of one of the formula (I)-(III) or a pharmaceutically acceptable salt thereof:

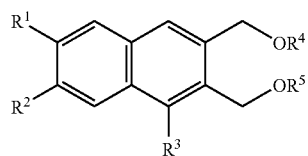
(I)

wherein $R^1$ and $R^2$ are the same or different and each a hydrogen atom, a hydroxyl group, a cyclo-lower alkyloxy group, or an optionally substituted lower alkoxy group, or bind together at the ends to form a lower alkylenedioxy group;

$R^3$ is an optionally substituted 6-membered nitrogen-containing heterocyclic group; and —$OR^4$ and —$OR^5$ are the same or different and each an optionally protected hydroxyl group;

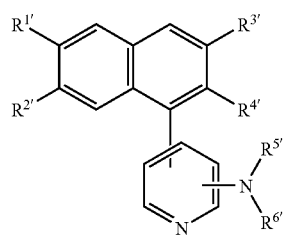
(II)

wherein $R^{1'}$ and $R^{2'}$ are the same or different and each a hydrogen atom or an optionally protected hydroxyl group;

either of $R^{3'}$ or $R^{4'}$ is an optionally protected hydroxy-substituted methyl group and the other is a hydrogen atom, a lower alkyl group or an optionally protected hydroxy-substituted methyl group; and $R^{5'}$ and $R^{6'}$ are the same or different and each a hydrogen atom, an optionally substituted lower alkyl group, an optionally substituted phenyl group or an optionally protected amino group, or bind together at the ends and form in association with the adjacent nitrogen atom an optionally substituted heterocyclic group;

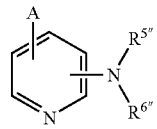
(III)

wherein A is a group selected from those shown by the formulas:

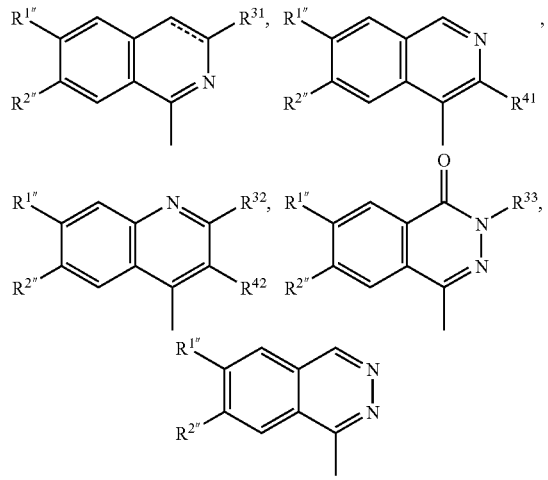

wherein $R^{1''}$ and $R^{2''}$ are the same or different and each a hydrogen atom or an optionally protected hydroxyl group;

$R^{31}$ is an optionally protected hydroxymethyl group; $R^{32}$ is a hydrogen atom, a lower alkyl group or an optionally protected hydroxymethyl group; $R^{33}$ is an optionally substituted lower alkyl group; $R^{41}$ is an optionally protected hydroxymethyl group; $R^{42}$ is an optionally protected hydroxymethyl group; the dotted line represents the presence or absence of a double bond; and $R^{5''}$ and $R^{6''}$ are the same or different and each a hydrogen atom or an optionally protected amino group, or bind together at the ends and form in association with the adjacent nitrogen atom an optionally substituted heterocyclic group.

21. The method according to claim 1, wherein the PDE4 inhibitor is one selected from the group consisting of Compounds (1 )-(57) or a pharmaceutically acceptable salt thereof:

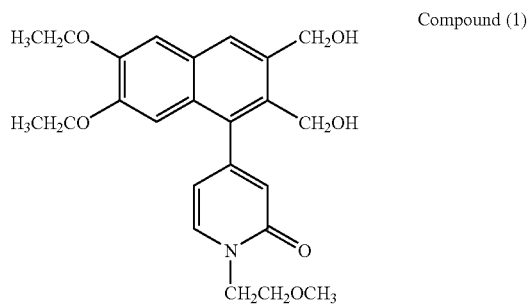
Compound (1)

-continued

Compound (2)

Compound (3)

Compound (4)

Compound (5)

Compound (6)

Compound (7)

-continued

Compound (8)

Compound (9)

Compound (10)

Compound (11)

Compound (12)

Compound (13)
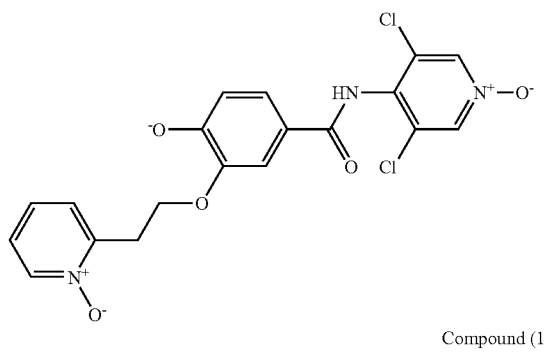
Compound (14)
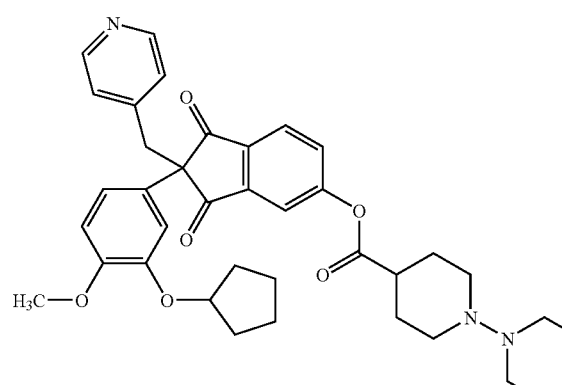
Compound (15)
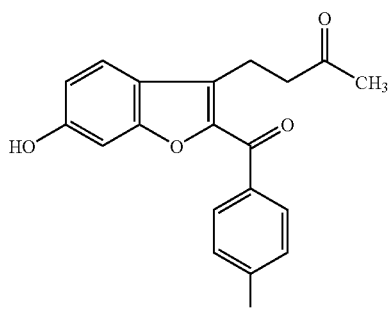
Compound (16)
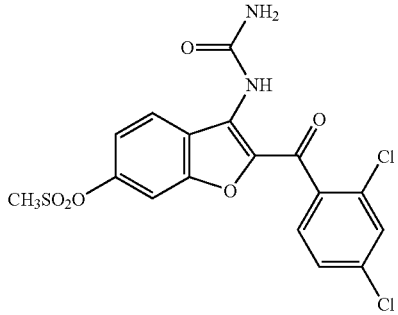
Compound (17)
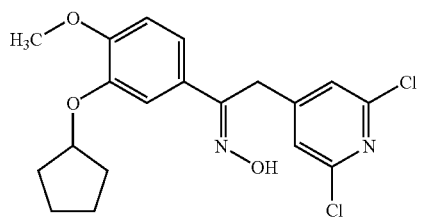
Compound (18)
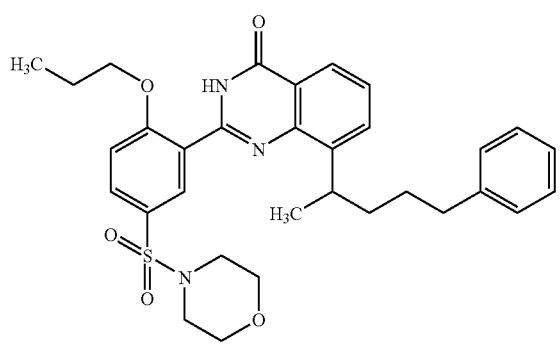
Compound (19)
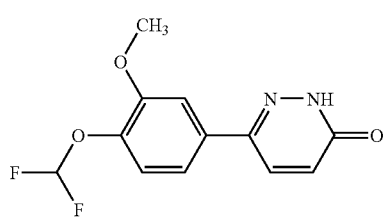
Compound (20)
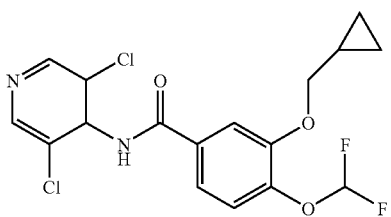
Compound (21)
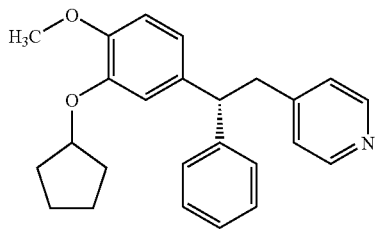
Compound (22)
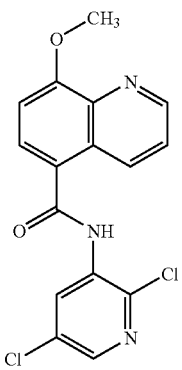

-continued
Compound (23)
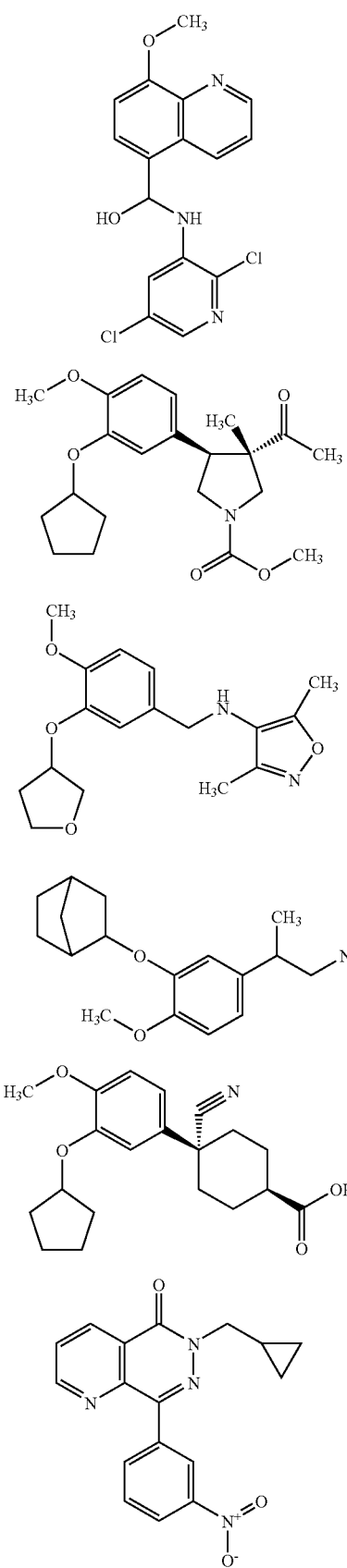
Compound (24)
Compound (25)
Compound (26)
Compound (27)
Compound (28)
-continued
Compound (29)
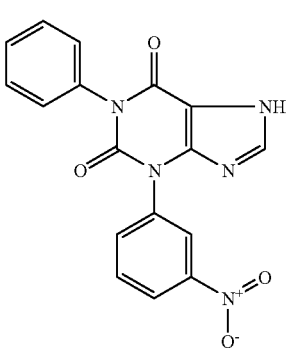
Compound (30)
Compound (31)
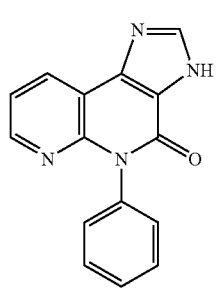
Compound (32)
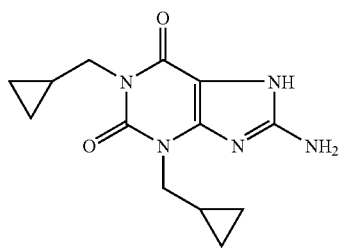
Compound (33)
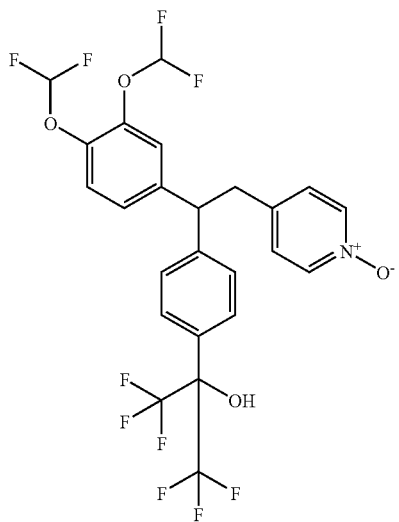

-continued
Compound (34)
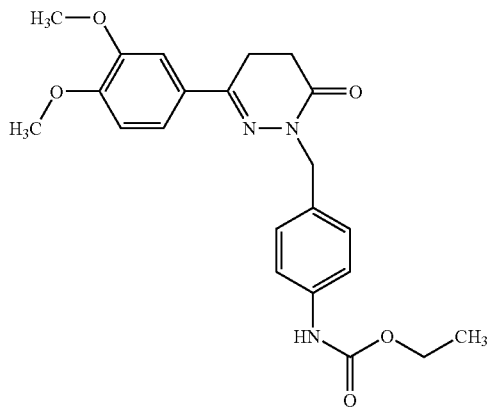
Compound (41)
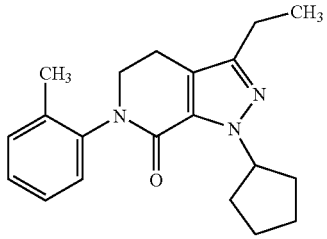
Compound (42)
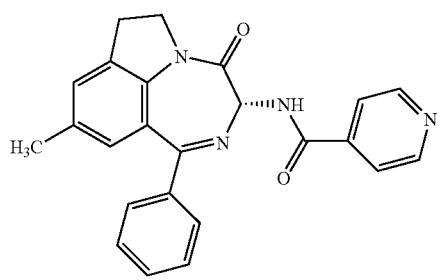
Compound (37)
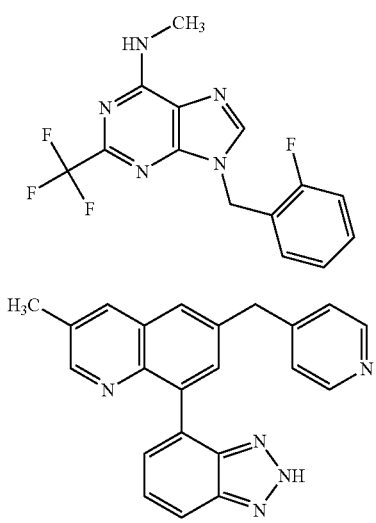
Compound (38)
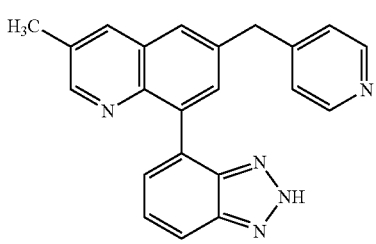
Compound (43)
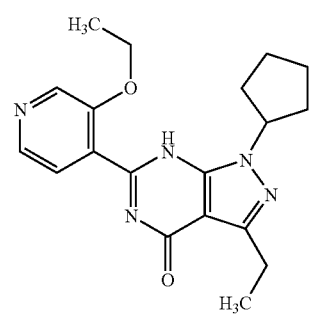
Compound (39)
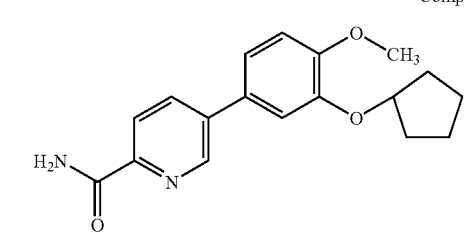
Compound (44)
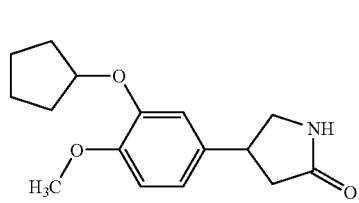
Compound (40)
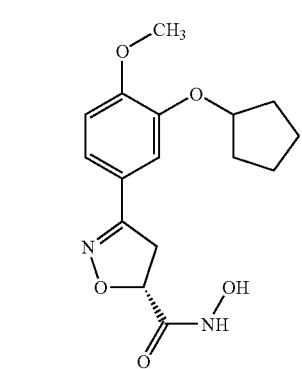
Compound (45)
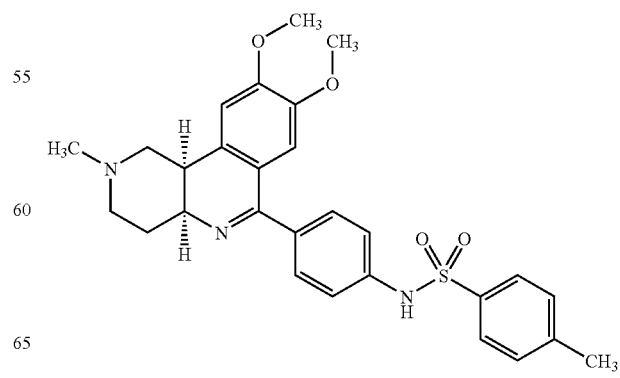

Compound (46)
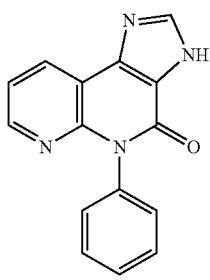
Compound (47)
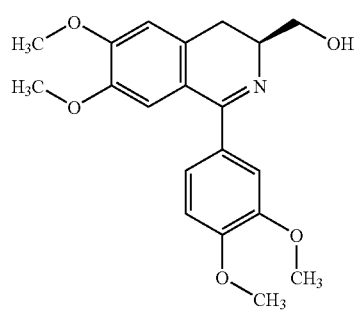
Compound (48)
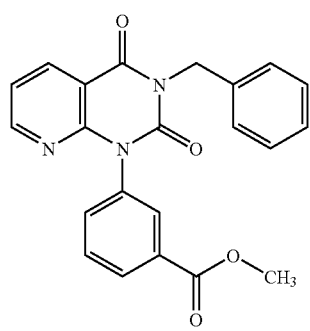
Compound (49)
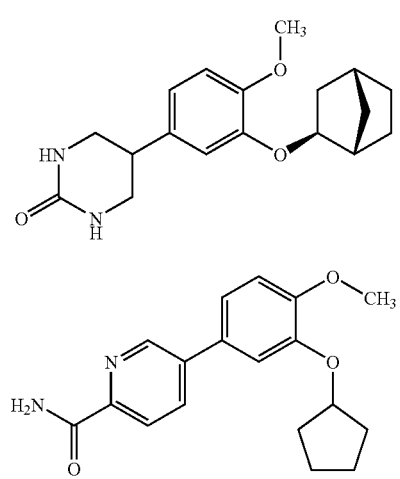
Compound (50)
Compound (51)
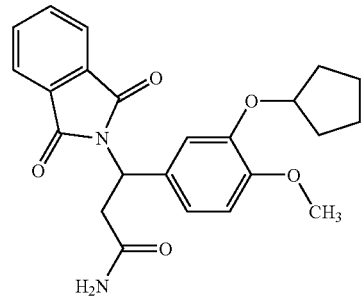
Compound (52)
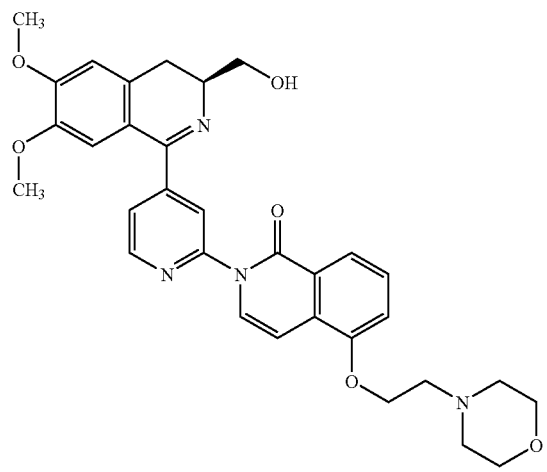
Compound (53)
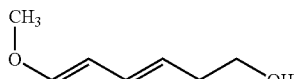

Compound (54)
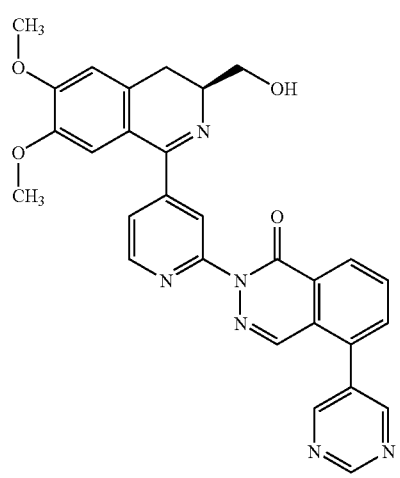
Compound (55)
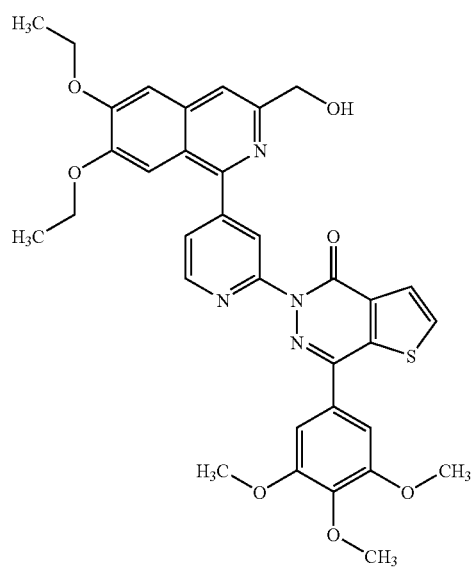
Compound (56)
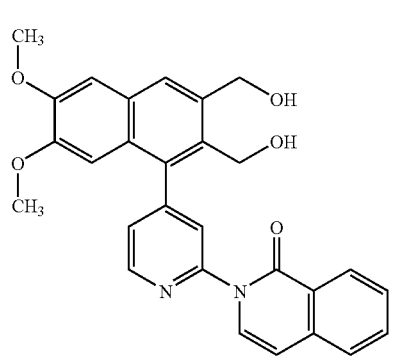
Compound (57)
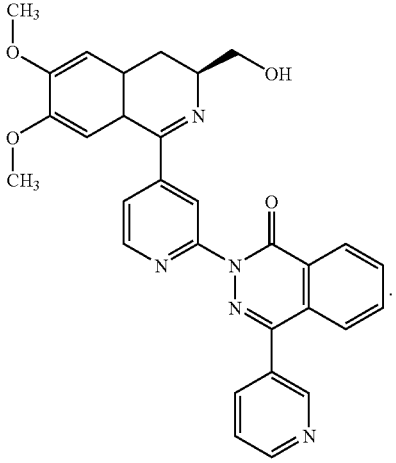
* * * * *